United States Patent [19]

Hamprecht et al.

[11] Patent Number: 4,829,072
[45] Date of Patent: May 9, 1989

[54] QUINOLINE DERIVATIVES MICROBICIDES CONTAINING THESE COMPOUNDS, AND THEIR USE FOR CONTROLLING BACTERIA AND FUNGI

[75] Inventors: Gerhard Hamprecht, Weinheim; Hans Theobald, Limburgerhof; Wolfgang Spiegler, Worms; Winfried Richarz, Stockstadt; Eberhard Ammermann, Ludwigshafen; Ernst-Heinrich Pommer, Limburgerhof, all of Fed. Rep. of Germany

[73] Assignee: BASF Aktiengesellschaft, Ludwigshafen, Fed. Rep. of Germany

[21] Appl. No.: 63,690

[22] Filed: Jun. 19, 1987

[30] Foreign Application Priority Data

Jun. 27, 1986 [DE] Fed. Rep. of Germany ....... 3621540

[51] Int. Cl.⁴ ................ C07D 401/12; C07D 409/12; C07D 413/12; C07D 417/12; C07D 419/12; A01N 43/42
[52] U.S. Cl. .................................... 514/314; 546/174; 546/175
[58] Field of Search ................. 546/174, 175; 514/314

[56] References Cited

U.S. PATENT DOCUMENTS 3,793,314  2/1974  Nardi et al. ...................... 546/178

FOREIGN PATENT DOCUMENTS 0098486  1/1984  European Pat. Off. .
3225169  1/1984  Fed. Rep. of Germany .
0095521  1/1971  France .
1141697  1/1969  United Kingdom .
1148405  4/1969  United Kingdom .

OTHER PUBLICATIONS

Massarani et al. (1975) Chemical Abstracts 82:57538d.
Kharizanova et al. (1973) Chemical Abstracts 79:27787e.

*Primary Examiner*—David B. Springer
*Attorney, Agent, or Firm*—Keil & Weinkauf

[57] ABSTRACT

Quinoline derivatives of the formula

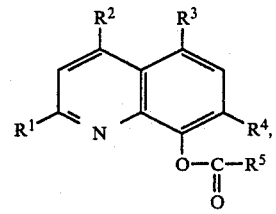

where $R^1$, $R^2$, $R^3$ and $R^4$ are hydrogen, methyl, halogen or nitro, $R^5$ is a thiophene, pyrrole, oxazole, thiazole, imidazole, isoxazole, isothiazole, pyrazole, thiadiazole, oxadiazole or triazole radical which is substituted or unsubstituted, or is a substituted furan radical, and microbicidal agents containing these compounds.

7 Claims, No Drawings

QUINOLINE DERIVATIVES MICROBICIDES CONTAINING THESE COMPOUNDS, AND THEIR USE FOR CONTROLLING BACTERIA AND FUNGI

The present invention relates to novel quinoline derivatives, processes for their preparation, microbicides which contain these compounds as active ingredients, and their use for controlling bacteria and fungi.

DE Nos. 3 225 169 and 2 005 959, GB No. 1 141 697 and EP-98 486 disclose that some 8-azolylcarbonyloxy-, 8-alphafuroyloxy- and 8-alpha-thenoyloxyquinoline derivatives can be used for controlling fungi, and some of them also for controlling bacteria. However, they do not always meet all the requirements, for example with regard to their microbicidal activity.

It is an object of the present invention to provide microbicidal compounds which are superior to the known ones in this respect.

We have found that this object is achieved, and that substituted quinoline derivatives of the formula

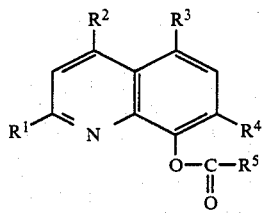

where $R^1$ is hydrogen or methyl, $R^2$ is hydrogen or halogen, $R^3$ is hydrogen, methyl, halogen or nitro, $R^4$ is hydrogen, halogen or nitro and $R^5$ is a thiophene, pyrrole, oxazole, thiazole, imidazole, isoxazole, isothiazole, pyrazole, 1,2,3-, 1,2,4-, 1,2,5- or 1,3,4-thiadiazole, 1,2,3-, 1,2,4-, 1,2,5- or 1,3,4-oxadiazole or 1,2,3- or 1,2,4-triazole radical which is unsubstituted or monosubstituted or disubstituted by $C_1$–$C_4$-alkyl, $C_1$–$C_4$-haloalkyl, nitro or halogen, the substituents being independent of one another in the case of disubstitution, or is furan which is substituted by halogen or monosubstituted or disubstituted by methyl, and $R^3$ and $R^4$ are not simultaneously halogen, with the exception of 5-chloro-, 2-methyl- and 5-nitro-8-(1',2',3'-thiadiazole-4'-carbonyloxy)-quinoline, 5-chloro-8-(4'-methyl-1',2',3'-thiadiazole-5'-carbonyloxy)-quinoline, 5-methyl-, 5-methyl-7-nitro-, 5-methyl-7-halo- and 7-nitro-8-(alpha-thenoyloxy)-quinoline, 5-nitro- and 5-methyl-7-nitro-8-(2'-halofuroyl-5'-oxy)quinoline and 2-methyl-8-(isoxazole-5'-carbonyloxy)-quinoline, possess excellent microbicidal activity.

The heterocyclic structure $R^5$ can be bonded to the remaining molecule at any possible position. $R^5$ is a thien-2-yl, thien-3-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, imidazol-1-yl, imidazol-2-yl, imidazol-4-yl, imidazol-5-yl, isoxazol-3-yl, isoxazol-4-yl, isoxazol-5-yl, isothiazol-3-yl, isothiazol-4-yl, isothiazol-5-yl, pyrazol-1-yl, pyrazol-3-yl, pyrazol-4-yl, pyrazol-5-yl, 1,3,4-thiadiazol-2-yl, 1,3,4-oxadiazol-2-yl, 1,2,4-thiadiazol-3-yl, 1,2,4-thiadiazol-5-yl, 1,2,4-oxadiazol-3-yl, 1,2,4-oxadiazol-5-yl, 1,2,4-triazol-1-yl, 1,2,4-triazol-3-yl, 1,2,4-triazol-5-yl, 1,2,3-thiadiazol-4-yl, 1,2,3-thiadiazol-5-yl, 1,2,3-oxadiazol-4-yl, 1,2,3-oxadiazol-5-yl, 1,2,3-triazol-1-yl, 1,2,3-triazol-4-yl, 1,2,3-triazol-5-yl, 1,2,5-thiadiazol-3-yl or 1,2,5-oxadiazol-3-yl radical which is unsubstituted or monosubstituted or disubstituted by $C_1$–$C_4$-haloalkyl, nitro or halogen, the substituents being independent of one another in the case of disubstitution, or is a furan-2-yl or furan-3-yl radical which is substituted by halogen or monosubstituted or disubstituted by methyl. Halogen is preferably chlorine or bromine.

Preferred compounds of the formula I are those in which $R^1$ is hydrogen, $R^2$ is hydrogen or halogen, $R^3$ is hydrogen, methyl, halogen or nitro, $R^4$ is hydrogen, halogen or nitro and $R^5$ is an unsubstituted or chloromethyl-substituted isoxazol-3-yl or isoxazol-5-yl radical, an unsubstituted or methyl-substituted oxazol-5-yl radical, an imidazol-1-yl radical or an unsubstituted or methyl-substituted 1,2,3-thiadiazol-4-yl or 1,2,3-thiadiazol-5-yl radical.

The compounds of the formula I are prepared, for example, by reacting a compound of the formula II

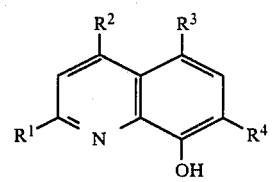

where $R^1$, $R^2$, $R^3$ and $R^4$ have the stated meanings, or one of its alkali metal or alkaline earth metal salts with a carboxylic acid derivative of the formula III

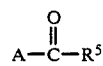

where $R^5$ has the above meanings and A is a nucleophilically displaceable leaving group.

In the formula III, A is, for example, halogen, such as chlorine or bromine, alkoxycarbonyloxy, such as methoxycarbonyloxy or ethoxycarbonyloxy, benzyloxycarbonyloxy, azolyl, such as imidazolyl or triazolyl, or alkoxy, such as methoxy or ethoxy.

In a variant, the quinoline derivatives of the formula I, where $R^5$ is azol-1-yl, can also be obtained by reacting a compound of the formula II, where $R^1$, $R^2$, $R^3$ and $R^4$ have the stated meanings, with a carbonylbisazole of the formula

where B is one of the azol-1-yl radicals stated in claim 1 for $R^5$.

Where carbonylbisimidazole and 8-hydroxyquinoline are used, the reaction can be represented by the following equation:

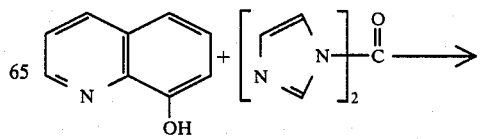

-continued

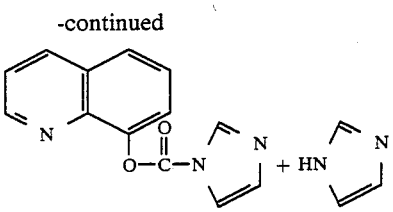

Although the reaction can also be carried out in the absence of solvents, it is advantageous to carry it out in an inert solvent or diluent. Examples of suitable solvents are:

halohydrocarbons, in particular chlorohydrocarbons, eg. tetrachloroethylene, 1,1,2,2- and 1,1,1,2-tetrachloroethane, dichloropropane, methylene chloride, dichlorobutane, chloroform, chloronaphthalene, dichloronaphthalene, carbon tetrachloride, 1,1,1- and 1,1,2-trichloroethane, trichloroethylene, pentachloroethane, o-, m- and p-difluorobenzene, 1,2-dichloroethane, 1,1-dichloroethane, 1,2-cis-dichloroethylene, chlorobenzene, fluorobenzene, bromobenzene, iodobenzene, o-, m- and p-dichlorobenzene, o-, p- and m-dibromobenzene, o-, m- and p-chlorotoluene or 1,2,4-trichlorobenzene; ethers, eg. ethyl propyl ether, methyl tert-butyl ether, n-butyl ether ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole or $\beta,\beta'$-dichlorodiethyl ether; nitrohydrocarbons, such as nitromethane, nitroethane, nitrobenzene, o-, m- and p-chloronitrobenzene or o-nitrotoluene; nitriles, such as acetonitrile, butyro- nitrile, isobutyronitrile, benzonitrile or m-chlorobenzonitrile; aliphatic and cycloaliphatic hydrocarbons, eg. heptane, pinane, nonane, o-, m- and p-cymene, gasoline fractions boiling within a range from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane or octane; esters, eg. ethyl acetate, ethyl acetoacetate or isobutyl acetate; amides, eg. formamide, methyl formamide or dimethyl formamide; ketones, eg. acetone or methyl ethyl ketone, and, if appropriate, also water and mixtures of these. Advantageously, the solvent is used in an amount of from 100 to 2000, preferably from 200 to 900, % by weight, based on starting material II.

Where A is halogen, it is advisable, although not essential, to carry out the reaction in the presence of an acid acceptor. Suitable acid acceptors are all conventional ones. These preferably include tertiary amines, alkaline earth metal compounds, ammonium compounds and alkali metal compounds, as well as mixtures of these. However, zinc compounds can also be used. Examples of suitable basic compounds are potassium hydroxide, sodium hydroxide, potassium carbonate, sodium carbonate, lithium hydroxide, lithium carbonate, sodium bicarbonate, potassium bicarbonate, calcium hydroxide, barium oxide, magnesium hydroxide, magnesium oxide, barium hydroxide, calcium carbonate, magnesium carbonate, magnesium acetate, zinc hydroxide, zinc oxide, zinc carbonate, zinc acetate, sodium formate, sodium acetate, trimethylamine, triethylamine, tripropylamine, triisopropylamine, tributylamine, triisobutylamine, tri-sec-butylamine, tri-tert-butylamine, tribenzylamine, tricyclohexylamine, triamylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N-methylpyrrolidone, N-ethylpyrrolidone, N-metylpiperidine, N-ethylpiperidine, N-methylpyrrolidine, N-ethylpyrrolidine, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, alpha-picoline, gamma-picoline, isoquinoline, pyrimidine, acridine, N,N,N'N'-tetramethylethylenediamine, N,N,N'N'-tetraethylethylenediamine, quinoxaline, quinazoline, N-propyldiisopropylamine, N,N-dimethylcyclohexylamine, 2,6-lutidine, 2,4-lutidine, trifurfurylamine and triethylenediamine.

The hydrogen halide, for example, formed during the reaction can, however, also be removed by passing in an inert gas, eg. nitrogen.

The process for the preparation of the novel compounds is advantageously carried out as follows: the starting material II, if necessary in one of the abovementioned diluents, is initially taken, and the starting material III or IV and, if required, an acid acceptor are then added simultaneously or in succession. However, it is also possible for the starting material III or IV in one of the abovementioned diluents to be initially taken and then the starting material II and, if required, an acid acceptor to be added, simultaneously or in any order, via two separate feeds.

In many cases, the reaction is complete as soon as the components have been added; in other cases, the reaction is completed by stirring for a further 10 minutes to 14 hours at from −10° to 120° C., preferably from 0° to 100° C., in particular from 20° to 80° C.

The compound I is isolated from the reaction mixture in a conventional manner, for example by distilling off the solvent or excess starting material III, or directly by filtration under suction. In this case, the remaining residue is washed with water or dilute alkali or acid in order to remove acidic or basic impurities, and is dried. In the case of water-immiscible diluents, the reaction mixture can also be extracted directly with water or with dilute alkali or acid and then dried and evaporated down. However, it is also possible to dissolve the residue in a water-immiscible solvent and to wash the solution as described above. The desired end products are obtained in pure form; if necessary, they can be further purified by recrystallization, chromatography or distillation.

In the Preparation Examples and Examples of use, parts and percentages are by weight.

Preparation Examples

EXAMPLE 1

5.1 parts of triethylamine were added to a stirred mixture of 13.5 parts of 7-bromo-5-nitro-8-hydroxyquinoline in 135 parts of ethyl acetate at from 15° to 25° C. in the course of 5 minutes, and the mixture was stirred for 5 minutes. 7.4 parts of 1,2,3-thiadiazole-4-carbonyl chloride were then added at from 20° to 25° C. in the course of 10 minutes, while stirring, and stirring was continued for 2 hours at 50° C. The reaction mixture was evaporated to dryness under reduced pressure, and the residue was dispersed in 400 parts of 0.5N hydrochloric acid in the course of 5 minutes. The undissolved material was filtered off under suction, and the filtrate was washed with water and stirred in 200 parts of 1N sodium hydroxide solution for 10 minutes. Filtration under suction, washing with water and drying gave 13 parts of 7-bromo-5-nitro-8-(1',2',3'-thiadiazole-4'-carbonyl)-oxyquinoline of melting point 192°-194° C.

EXAMPLE 2

6.52 parts of 2-methylpyridine were added to a stirred mixture of 15.7 parts of 7-chloro-5-nitro-8-hydroxyquinoline in 190 parts of 1,2-dichloroethane at 25° C. in the course of 5 minutes, and the mixture was stirred for 5 minutes. 9.2 parts of isoxazole-5-carbonyl chloride were then added at from 20° to 25° C. in the course of 10 minutes, while stirring, and stirring was continued for 3 hours at 55° C. The reaction mixture was evaporated to dryness under reduced pressure, and the residue was stirred in 200 parts of 0.5N hydrochloric acid for 5 minutes. The precipitate was filtered off under suction, washed with water and stirred for 10 minutes in 200 parts of dilute sodium carbonate solution. Filtration under suction, washing with water at 60° C. and drying gave 17.5 parts of 7-chloro-5-nitro-8-(isoxazole-5'-carbonyl)-oxyquinoline of melting point 132°-134° C.

EXAMPLE 3

29 parts of 8-hydroxyquinoline in 65 parts of tetrahydrofuran were added to a stirred solution of 32.4 parts of 1,1-carbonylbisimidazole in 120 parts of tetrahydrofuran at from 20° to 25° C. in the course of 3 minutes, and the mixture was stirred for 12 hours at room temperature. The precipitate which separated out was filtered off under suction, washed with diethyl ether and water in succession and dried. 21 parts of 8-(imidazole-1'-carbonyl)-oxyquinoline of melting point 137°-141° C. were obtained.

The following Examples can be prepared in a similar manner:

| No. | $R^1$ | $R^2$ | $R^3$ | $R^4$ | $R^5$ | m.p. [°C.] |
|---|---|---|---|---|---|---|
| 4 | H | H | H | Cl | thenyl-2 | |
| 5 | H | H | H | Cl | thenyl-3 | |
| 6 | H | H | H | Cl | 2-chlorothenyl-3 | |
| 7 | H | H | H | Cl | 5-chlorothenyl-2 | |
| 8 | H | H | H | Cl | 5-nitrothenyl-2 | |
| 9 | H | H | H | Cl | 4-methylthenyl-2 | |
| 10 | H | H | H | Cl | 3-methylthenyl-2 | |
| 11 | H | H | H | Cl | 2-methylthenyl-3 | |
| 12 | H | H | H | Cl | 3-methylthenyl-4 | |
| 13 | H | H | H | Cl | 2,5-dimethylthenyl-4 | |
| 14 | H | H | H | Cl | 2,3-dichlorothenyl-4 | |
| 15 | H | H | H | Cl | 5-methylthenyl-2 | |
| 16 | H | H | H | Cl | pyrryl-2 | |
| 17 | H | H | H | Cl | pyrryl-3 | |
| 18 | H | H | H | Cl | 3-methylpyrryl-2 | |
| 19 | H | H | H | Cl | 2-methylpyrryl-3 | |
| 20 | H | H | H | Cl | 5-chloropyrryl-2 | |
| 21 | H | H | H | Cl | oxazolyl-2 | |
| 22 | H | H | H | Cl | oxazolyl-4 | |
| 23 | H | H | H | Cl | oxazolyl-5 | |
| 24 | H | H | H | Cl | 1,2,3-thiadiazolyl-4 | 121–123 |
| 25 | H | H | H | Cl | 4-methyloxazolyl-5 | |
| 26 | H | H | H | Cl | 2-methyloxazolyl-5 | |
| 27 | H | H | H | Cl | thiazolyl-2 | |
| 28 | H | H | H | Cl | thiazolyl-4 | |
| 29 | H | H | H | Cl | thiazolyl-5 | |
| 30 | H | H | H | Cl | 4-methylthiazolyl-5 | |
| 31 | H | H | H | Cl | 2-methylthiazolyl-5 | |
| 32 | H | H | H | Cl | imidazolyl-4 | |
| 33 | H | H | H | Cl | imidazolyl-5 | |
| 34 | H | H | H | Cl | 4-methylimidazolyl-5 | |
| 35 | H | H | H | Cl | 1-methylimidazolyl-5 | |
| 36 | H | H | H | Cl | 4-nitroimidazolyl-1 | |
| 37 | H | H | H | Cl | 2-methyl-4-nitroimidazolyl-1 | |
| 38 | H | H | H | Cl | 4,5-dichloroimidazolyl-1 | |
| 39 | H | H | H | Cl | 1-methylpyrryl-2 | |
| 40 | H | H | H | Cl | isoxazolyl-3 | 93–96 |
| 41 | H | H | H | Cl | isoxazolyl-4 | |
| 42 | H | H | H | Cl | isoxazolyl-5 | 101–104 |
| 43 | H | H | H | Cl | 5-chloromethylisoxazolyl-3 | 151–152 |
| 44 | H | H | H | Cl | isothiazolyl-3 | |
| 45 | H | H | H | Cl | isothiazolyl-4 | |
| 46 | H | H | H | Cl | isothiazolyl-5 | |
| 47 | H | H | H | Cl | 4-methylisothiazolyl-5 | |
| 48 | H | H | H | Cl | pyrazolyl-4 | |
| 49 | H | H | H | Cl | pyrazolyl-5 | |
| 50 | H | H | H | Cl | 4-chloropyrazolyl-5 | |
| 51 | H | H | H | Cl | 1-methylpyrazolyl-5 | |
| 52 | H | H | H | Cl | 1,2,3-thiadiazolyl-5 | |
| 53 | H | H | H | Cl | 1,2,3-oxadiazolyl-5 | |
| 54 | H | H | H | Cl | 1,2,3-oxadiazolyl-4 | |
| 55 | H | H | H | Cl | 5-methyl-1,2,3-oxadiazolyl-4 | |
| 56 | H | H | H | Cl | 4-methyl-1,2,3-oxadiazolyl-5 | |
| 57 | H | H | H | Cl | 1,3,4-thiadiazolyl-2 | |
| 58 | H | H | H | Cl | 2-methyl-1,3,4-thiadiazolyl-5 | |
| 59 | H | H | H | Cl | 1,2,4-thiadiazolyl-3 | |
| 60 | H | H | H | Cl | 1,2,4-thiadiazolyl-5 | |
| 61 | H | H | H | Cl | 3-methyl-1,2,4-thiadiazolyl-5 | |

-continued

| No. | R¹ | R² | R³ | R⁴ | R⁵ | m.p. [°C.] |
|---|---|---|---|---|---|---|
| 62 | H | H | H | Cl | 1,2,4-oxadiazolyl-3 | |
| 63 | H | H | H | Cl | 1,2,4-oxadiazolyl-5 | |
| 64 | H | H | H | Cl | 1,2,4-triazolyl-5 | |
| 65 | H | H | H | Cl | 1,2,4-triazolyl-3 | |
| 66 | H | H | H | Cl | 1,3,4-oxadiazolyl-5 | |
| 67 | H | H | H | Cl | 2-methyl-1,3,4-oxadiazolyl-5 | |
| 68 | H | H | H | Cl | 2-chloro-1,3,4-oxadiazolyl-5 | |
| 69 | H | H | H | Cl | 1,2,5-oxadiazolyl-3 | |
| 70 | H | H | H | Cl | 3-methyl-1,2,5-oxadiazolyl-4 | |
| 71 | H | H | H | Cl | 1,2,5-thiadiazolyl-3 | |
| 72 | H | H | H | Cl | 3-methyl-1,2,5-thiadiazolyl-4 | |
| 73 | H | H | H | Cl | 2-methylfuryl-5 | |
| 74 | H | H | H | Cl | 2,5-dimethylfuryl-4 | 111–114 |
| 75 | H | H | H | Cl | 2-chlorofuryl-5 | |
| 76 | H | H | H | Cl | 5-methyloxazolyl-4 | |
| 77 | H | H | H | Cl | 4-methyloxazolyl-2 | |
| 78 | H | H | H | Cl | 2-bromofuryl-5 | |
| 79 | H | H | H | Cl | 2-methylfuryl-4 | |
| 80 | H | H | H | Cl | 5-methylisoxazolyl-3 | |
| 81 | H | H | H | Cl | 4-methylisoxazolyl-3 | |
| 82 | H | H | H | Cl | 5-methylisothiazolyl-3 | |
| 83 | H | H | H | Cl | 4-methylisothiazolyl-3 | |
| 84 | H | H | H | Cl | 5-methyl-1,2,3-thiadiazolyl-4 | |
| 85 | H | H | H | Cl | 4-methyl-1,2,3-thiadiazolyl-5 | 162–164 |
| 86 | H | H | H | Cl | pyrryl-1 | |
| 87 | H | H | H | Cl | imidazolyl-1 | |
| 88 | H | H | H | Cl | pyrazolyl-1 | |
| 89 | H | H | H | Cl | 1,3,4-triazolyl-1 | |
| 90 | H | H | H | Cl | 1,2,4-triazolyl-1 | |
| 91 | H | H | H | Br | thenyl-2 | |
| 92 | H | H | H | Br | thenyl-3 | |
| 93 | H | H | H | Br | 2-chlorothenyl-3 | |
| 94 | H | H | H | Br | 5-chlorothenyl-2 | |
| 95 | H | H | H | Br | 5-nitrothenyl-2 | |
| 96 | H | H | H | Br | 4-methylthenyl-2 | |
| 97 | H | H | H | Br | 3-methylthenyl-2 | |
| 98 | H | H | H | Br | 2-methylthenyl-3 | |
| 99 | H | H | H | Br | 3-methylthenyl-4 | |
| 100 | H | H | H | Br | 2,5-dimethylthenyl-4 | |
| 101 | H | H | H | Br | 2,3-dichlorothenyl-4 | |
| 102 | H | H | H | Br | 5-methylthenyl-2 | |
| 103 | H | H | H | Br | pyrryl-2 | |
| 104 | H | H | H | Br | pyrryl-3 | |
| 105 | H | H | H | Br | 3-methylpyrryl-2 | |
| 106 | H | H | H | Br | 2-methylpyrryl-3 | |
| 107 | H | H | H | Br | 5-chloropyrryl-2 | |
| 108 | H | H | H | Br | oxazolyl-2 | |
| 109 | H | H | H | Br | oxazolyl-4 | |
| 110 | H | H | H | Br | oxazolyl-5 | |
| 111 | H | H | H | Br | 1,2,3-thiadiazolyl-4 | 127–130 |
| 112 | H | H | H | Br | 4-methyloxazolyl-5 | |
| 113 | H | H | H | Br | 2-methyloxazolyl-5 | |
| 114 | H | H | H | Br | thiazolyl-2 | |
| 115 | H | H | H | Br | thiazolyl-4 | |
| 116 | H | H | H | Br | thiazolyl-5 | |
| 117 | H | H | H | Br | 4-methylthiazolyl-5 | |
| 118 | H | H | H | Br | 2-methylthiazolyl-5 | |
| 119 | H | H | H | Br | imidazolyl-4 | |
| 120 | H | H | H | Br | imidazolyl-5 | |
| 121 | H | H | H | Br | 4-methylimidazolyl-5 | |
| 122 | H | H | H | Br | 1-methylimidazolyl-5 | |
| 123 | H | H | H | Br | 4-nitroimidazolyl-1 | |
| 124 | H | H | H | Br | 2-methyl-4-nitroimidazolyl-1 | |
| 125 | H | H | H | Br | 4,5-dichloroimidazolyl-1 | |
| 126 | H | H | H | Br | 1-methylpyrryl-2 | |
| 127 | H | H | H | Br | isoxazolyl-3 | 126–128 |
| 128 | H | H | H | Br | isoxazolyl-4 | |
| 129 | H | H | H | Br | isoxazolyl-5 | |
| 130 | H | H | H | Br | 5-chloromethylisoxazolyl-3 | 148–151 |
| 131 | H | H | H | Br | isothiazolyl-3 | |
| 132 | H | H | H | Br | isothiazolyl-4 | |
| 133 | H | H | H | Br | isothiazolyl-5 | |
| 134 | H | H | H | Br | 4-methylisothiazolyl-5 | |
| 135 | H | H | H | Br | pyrazolyl-4 | |
| 136 | H | H | H | Br | pyrazolyl-5 | |
| 137 | H | H | H | Br | 4-chloropyrazolyl-5 | |
| 138 | H | H | H | Br | 1-methylpyrazolyl-5 | |
| 139 | H | H | H | Br | 1,2,3-thiadiazolyl-5 | |
| 140 | H | H | H | Br | 1,2,3-oxadiazolyl-5 | |
| 141 | H | H | H | Br | 1,2,3-oxadiazolyl-4 | |
| 142 | H | H | H | Br | 5-methyl-1,2,3-oxadiazolyl-4 | |

-continued

| No. | R¹ | R² | R³ | R⁴ | R⁵ | m.p. [°C.] |
|---|---|---|---|---|---|---|
| 143 | H | H | H | Br | 4-methyl-1,2,3-oxadiazolyl-5 | |
| 144 | H | H | H | Br | 1,3,4-thiadiazolyl-2 | |
| 145 | H | H | H | Br | 2-methyl-1,3,4-thiadiazolyl-5 | |
| 146 | H | H | H | Br | 1,2,4-thiadiazolyl-3 | |
| 147 | H | H | H | Br | 1,2,4-thiadiazolyl-5 | |
| 148 | H | H | H | Br | 3-methyl-1,2,4-thiadiazolyl-5 | |
| 149 | H | H | H | Br | 1,2,4-oxadiazolyl-3 | |
| 150 | H | H | H | Br | 1,2,4-oxadiazolyl-5 | |
| 151 | H | H | H | Br | 1,2,4-triazolyl-5 | |
| 152 | H | H | H | Br | 1,2,4-triazolyl-3 | |
| 153 | H | H | H | Br | 1,3,4-oxadiazolyl-5 | |
| 154 | H | H | H | Br | 2-methyl-1,3,4-oxadiazolyl-5 | |
| 155 | H | H | H | Br | 2-chloro-1,3,4-oxadiazolyl-5 | |
| 156 | H | H | H | Br | 1,2,5-oxadiazolyl-3 | |
| 157 | H | H | H | Br | 3-methyl-1,2,5-oxadiazolyl-4 | |
| 158 | H | H | H | Br | 1,2,5-thiadiazolyl-3 | |
| 159 | H | H | H | Br | 3-methyl-1,2,5-thiadiazolyl-4 | |
| 160 | H | H | H | Br | 2-methyl-furyl-5 | |
| 161 | H | H | H | Br | 2,5-dimethylfuryl-4 | 159–161 |
| 162 | H | H | H | Br | 2-chlorofuryl-5 | |
| 163 | H | H | H | Br | 5-methyl-oxazolyl-4 | |
| 164 | H | H | H | Br | 4-methyl-oxazolyl-2 | |
| 165 | H | H | H | Br | 2-bromofuryl-5 | |
| 166 | H | H | H | Br | 2-methylfuryl-4 | |
| 167 | H | H | H | Br | 5-methylisoxazolyl-3 | |
| 168 | H | H | H | Br | 4-methylisoxazolyl-3 | |
| 169 | H | H | H | Br | 5-methylisothiazolyl-3 | |
| 170 | H | H | H | Br | 4-methylisothiazolyl-3 | |
| 171 | H | H | H | Br | 5-methyl-1,2,3-thiadiazolyl-4 | |
| 172 | H | H | H | Br | 4-methyl-1,2,3-thiadiazolyl-5 | 184–185 |
| 173 | H | H | H | Br | pyrryl-1 | |
| 174 | H | H | H | Br | imidazolyl-1 | |
| 175 | H | H | H | Br | pyrazolyl-1 | |
| 176 | H | H | H | Br | 1,3,4-triazolyl-1 | |
| 177 | H | H | H | Br | 1,2,4-triazolyl-1 | |
| 178 | H | H | H | NO₂ | 2-chlorothenyl-3 | |
| 179 | H | H | H | NO₂ | 5-chlorothenyl-2 | |
| 180 | H | H | H | NO₂ | 5-nitrothenyl-2 | |
| 181 | H | H | H | NO₂ | 4-methylthenyl-2 | |
| 182 | H | H | H | NO₂ | 3-methylthenyl-2 | |
| 183 | H | H | H | NO₂ | 2-methylthenyl-3 | |
| 184 | H | H | H | NO₂ | 3-methylthenyl-4 | |
| 185 | H | H | H | NO₂ | 2,5-dimethylthenyl-4 | |
| 186 | H | H | H | NO₂ | 2,3-dichlorothenyl-4 | |
| 187 | H | H | H | NO₂ | 5-methylthenyl-2 | |
| 188 | H | H | H | NO₂ | pyrryl-2 | |
| 189 | H | H | H | NO₂ | pyrryl-3 | |
| 190 | H | H | H | NO₂ | 3-methylpyrryl-2 | |
| 191 | H | H | H | NO₂ | 2-methylpyrryl-3 | |
| 192 | H | H | H | NO₂ | 5-chloropyrryl-2 | |
| 193 | H | H | H | NO₂ | oxazolyl-2 | |
| 194 | H | H | H | NO₂ | oxazolyl-4 | |
| 195 | H | H | H | NO₂ | oxazolyl-5 | |
| 196 | H | H | H | NO₂ | 1,2,3-thiadiazolyl-4 | 198 Decomp. |
| 197 | H | H | H | NO₂ | 4-methyloxazolyl-5 | |
| 198 | H | H | H | NO₂ | 2-methyloxazolyl-5 | |
| 199 | H | H | H | NO₂ | thiazolyl-2 | |
| 200 | H | H | H | NO₂ | thiazolyl-4 | |
| 201 | H | H | H | NO₂ | thiazolyl-5 | |
| 202 | H | H | H | NO₂ | 4-methylthiazolyl-5 | |
| 203 | H | H | H | NO₂ | 2-methylthiazolyl-5 | |
| 204 | H | H | H | NO₂ | imidazolyl-4 | |
| 205 | H | H | H | NO₂ | imidazolyl-5 | |
| 206 | H | H | H | NO₂ | 4-methylimidazolyl-5 | |
| 207 | H | H | H | NO₂ | 1-methylimidazolyl-5 | |
| 208 | H | H | H | NO₂ | 4-nitroimidazolyl-1 | |
| 209 | H | H | H | NO₂ | 2-methyl-4-nitroimidazolyl-1 | |
| 210 | H | H | H | NO₂ | 4,5-dichloroimidazolyl-1 | |
| 211 | H | H | H | NO₂ | 1-methylpyrryl-2 | |
| 212 | H | H | H | NO₂ | isoxazolyl-5 | 153–154 |
| 213 | H | H | H | NO₂ | isoxazolyl-4 | |
| 214 | H | H | H | NO₂ | isoxazolyl-5 | 168–170 |
| 215 | H | H | H | NO₂ | 5-chloromethylisoxazolyl-3 | 129–131 |
| 216 | H | H | H | NO₂ | isothiazolyl-3 | |
| 217 | H | H | H | NO₂ | isothiazolyl-4 | |
| 218 | H | H | H | NO₂ | isothiazolyl-5 | |
| 219 | H | H | H | NO₂ | 4-methylisothiazolyl-5 | |
| 220 | H | H | H | NO₂ | pyrazolyl-4 | |
| 221 | H | H | H | NO₂ | pyrazolyl-5 | |
| 222 | H | H | H | NO₂ | 4-chloropyrazolyl-5 | |
| 223 | H | H | H | NO₂ | 1-methylpyrazolyl-5 | |

-continued

| No. | R¹ | R² | R³ | R⁴ | R⁵ | m.p. [°C.] |
|---|---|---|---|---|---|---|
| 224 | H | H | H | NO₂ | 1,2,3-thiadiazolyl-5 | |
| 225 | H | H | H | NO₂ | 1,2,3-oxadiazolyl-5 | |
| 226 | H | H | H | NO₂ | 1,2,3-oxadiazolyl-4 | |
| 227 | H | H | H | NO₂ | 5-methyl-1,2,3-oxadiazolyl-4 | |
| 228 | H | H | H | NO₂ | 4-methyl-1,2,3-oxadiazolyl-5 | |
| 229 | H | H | H | NO₂ | 1,3,4-thiadiazolyl-2 | |
| 230 | H | H | H | NO₂ | 2-methyl-1,3,4-thiadiazolyl-5 | |
| 231 | H | H | H | NO₂ | 1,2,4-thiadiazolyl-3 | |
| 232 | H | H | H | NO₂ | 1,2,4-thiadiazolyl-5 | |
| 233 | H | H | H | NO₂ | 3-methyl-1,2,4-thiadiazolyl-5 | |
| 234 | H | H | H | NO₂ | 1,2,4-oxadiazolyl-3 | |
| 235 | H | H | H | NO₂ | 1,2,4-oxadiazolyl-5 | |
| 236 | H | H | H | NO₂ | 1,2,4-triazolyl-5 | |
| 237 | H | H | H | NO₂ | 1,2,4-triazolyl-3 | |
| 238 | H | H | H | NO₂ | 1,3,4-oxadiazolyl-5 | |
| 239 | H | H | H | NO₂ | 2-methyl-1,3,4-oxadiazolyl-5 | |
| 240 | H | H | H | NO₂ | 2-chloro-1,3,4-oxadiazolyl-5 | |
| 241 | H | H | H | NO₂ | 1,2,5-oxadiazolyl-3 | |
| 242 | H | H | H | NO₂ | 3-methyl-1,2,5-oxadiazolyl-4 | |
| 243 | H | H | H | NO₂ | 1,2,5-thiadiazolyl-3 | |
| 244 | H | H | H | NO₂ | 3-methyl-1,2,5-thiadiazolyl-4 | |
| 245 | H | H | H | NO₂ | 2-methylfuryl-5 | |
| 246 | H | H | H | NO₂ | 2,5-dimethylfuryl-4 | 156–157 |
| 247 | H | H | H | NO₂ | 2-chlorofuryl-5 | |
| 248 | H | H | H | NO₂ | 5-methyloxazolyl-4 | |
| 249 | H | H | H | NO₂ | 4-methyloxazolyl-2 | |
| 250 | H | H | H | NO₂ | 2-bromofuryl-5 | |
| 251 | H | H | H | NO₂ | 2-methylfuryl-4 | |
| 252 | H | H | H | NO₂ | 5-methylisoxazolyl-3 | |
| 253 | H | H | H | NO₂ | 4-methylisoxazolyl-3 | |
| 254 | H | H | H | NO₂ | 5-methylisothiazolyl-3 | |
| 255 | H | H | H | NO₂ | 4-methylisothiazolyl-3 | |
| 256 | H | H | H | NO₂ | 4-methyl-1,2,3-thiadiazolyl-5 | 154–155 |
| 257 | H | H | H | NO₂ | 5-methyl-1,2,3-thiadiazolyl-4 | |
| 258 | H | H | H | NO₂ | pyrryl-1 | |
| 259 | H | H | H | NO₂ | imidazolyl-1 | |
| 260 | H | H | H | NO₂ | pyrazolyl-1 | |
| 261 | H | H | H | NO₂ | 1,3,4-triazolyl-1 | |
| 262 | H | H | H | NO₂ | 1,2,4-triazolyl-1 | |
| 263 | H | H | NO₂ | H | thenyl-2 | |
| 264 | H | H | NO₂ | H | thenyl-3 | |
| 265 | H | H | NO₂ | H | 2-chlorothenyl-3 | |
| 266 | H | H | NO₂ | H | 5-chlorothenyl-2 | |
| 267 | H | H | NO₂ | H | 5-nitrothenyl-2 | |
| 268 | H | H | NO₂ | H | 4-methylthenyl-2 | |
| 269 | H | H | NO₂ | H | 3-methylthenyl-2 | |
| 270 | H | H | NO₂ | H | 2-methylthenyl-3 | |
| 271 | H | H | NO₂ | H | 3-methylthenyl-4 | |
| 272 | H | H | NO₂ | H | 2,5-dimethylthenyl-4 | |
| 273 | H | H | NO₂ | H | 2,3-dichlorothenyl-4 | |
| 274 | H | H | NO₂ | H | 5-methylthenyl-2 | |
| 275 | H | H | NO₂ | H | pyrryl-2 | |
| 276 | H | H | NO₂ | H | pyrryl-3 | |
| 277 | H | H | NO₂ | H | 3-methylpyrryl-2 | |
| 278 | H | H | NO₂ | H | 2-methylpyrryl-3 | |
| 279 | H | H | NO₂ | H | 5-chloropyrryl-2 | |
| 280 | H | H | NO₂ | H | oxazolyl-2 | |
| 281 | H | H | NO₂ | H | oxazolyl-4 | |
| 282 | H | H | NO₂ | H | oxazolyl-5 | |
| 283 | H | H | NO₂ | H | 4-methyloxazolyl-5 | |
| 284 | H | H | NO₂ | H | 2-methyloxazolyl-5 | |
| 285 | H | H | NO₂ | H | thiazolyl-2 | |
| 286 | H | H | NO₂ | H | thiazolyl-4 | |
| 287 | H | H | NO₂ | H | thiazolyl-5 | |
| 288 | H | H | NO₂ | H | 4-methylthiazolyl-5 | |
| 289 | H | H | NO₂ | H | 2-methylthiazolyl-5 | |
| 290 | H | H | NO₂ | H | imidazolyl-4 | |
| 291 | H | H | NO₂ | H | imidazolyl-5 | |
| 292 | H | H | NO₂ | H | 4-methylimidazolyl-5 | |
| 293 | H | H | NO₂ | H | 1-methylimidazolyl-5 | |
| 294 | H | H | NO₂ | H | 4-nitroimidazolyl-1 | |
| 295 | H | H | NO₂ | H | 2-methyl-4-nitroimidazolyl-1 | |
| 296 | H | H | NO₂ | H | 4,5-dichloroimidazolyl-1 | |
| 297 | H | H | NO₂ | H | 1-methylpyrryl-2 | |
| 298 | H | H | NO₂ | H | isoxazolyl-3 | 150–152 |
| 299 | H | H | NO₂ | H | isoxazolyl-4 | |
| 300 | H | H | NO₂ | H | isoxazolyl-5 | 167–169 |
| 301 | H | H | NO₂ | H | 5-chloromethylisoxazolyl-3 | 129–131 |
| 302 | H | H | NO₂ | H | isothiazolyl-3 | |
| 303 | H | H | NO₂ | H | isothiazolyl-4 | |
| 304 | H | H | NO₂ | H | isothiazolyl-5 | |

-continued

| No. | R¹ | R² | R³ | R⁴ | R⁵ | m.p. [°C.] |
|---|---|---|---|---|---|---|
| 305 | H | H | NO₂ | H | 4-methylisothiazolyl-5 | |
| 306 | H | H | NO₂ | H | pyrazolyl-4 | |
| 307 | H | H | NO₂ | H | pyrazolyl-5 | |
| 308 | H | H | NO₂ | H | 4-chloropyrazolyl-5 | |
| 309 | H | H | NO₂ | H | 1-methylpyrazolyl-5 | |
| 310 | H | H | NO₂ | H | 1,2,3-thiadiazolyl-5 | |
| 311 | H | H | NO₂ | H | 1,2,3-oxadiazolyl-5 | |
| 312 | H | H | NO₂ | H | 1,2,3-oxadiazolyl-4 | |
| 313 | H | H | NO₂ | H | 5-methyl-1,2,3-oxadiazolyl-4 | |
| 314 | H | H | NO₂ | H | 4-methyl-1,2,3-oxadiazolyl-5 | |
| 315 | H | H | NO₂ | H | 1,3,4-thiadiazolyl-2 | |
| 316 | H | H | NO₂ | H | 2-methyl-1,3,4-thiadiazolyl-5 | |
| 317 | H | H | NO₂ | H | 1,2,4-thiadiazolyl-3 | |
| 318 | H | H | NO₂ | H | 1,2,4-thiadiazolyl-5 | |
| 319 | H | H | NO₂ | H | 3-methyl-1,2,4-thiadiazolyl-5 | |
| 320 | H | H | NO₂ | H | 1,2,4-oxadiazolyl-3 | |
| 321 | H | H | NO₂ | H | 1,2,4-oxadiazolyl-5 | |
| 322 | H | H | NO₂ | H | 1,2,4-triazolyl-5 | |
| 323 | H | H | NO₂ | H | 1,2,4-triazolyl-3 | |
| 324 | H | H | NO₂ | H | 1,3,4-oxadiazolyl-5 | |
| 325 | H | H | NO₂ | H | 2-methyl-1,3,4-oxadiazolyl-5 | |
| 326 | H | H | NO₂ | H | 2-chloro-1,3,4-oxadiazolyl-5 | |
| 327 | H | H | NO₂ | H | 1,2,5-oxadiazolyl-3 | |
| 328 | H | H | NO₂ | H | 3-methyl-1,2,5-oxadiazolyl-4 | |
| 329 | H | H | NO₂ | H | 1,2,5-thiadiazolyl-3 | |
| 330 | H | H | NO₂ | H | 3-methyl-1,2,5-thiadiazolyl-4 | |
| 331 | H | H | NO₂ | H | 2-methylfuryl-5 | |
| 332 | H | H | NO₂ | H | 2,5-dimethylfuryl | 158–160 |
| 333 | H | H | NO₂ | H | 5-methyloxazolyl-4 | |
| 334 | H | H | NO₂ | H | 4-methyloxazolyl-2 | |
| 335 | H | H | NO₂ | H | 2-bromofuryl-5 | |
| 336 | H | H | NO₂ | H | 2-methylfuryl-4 | |
| 337 | H | H | NO₂ | H | 5-methylisoxazolyl-3 | |
| 338 | H | H | NO₂ | H | 4-methylisoxazolyl-3 | |
| 339 | H | H | NO₂ | H | 5-methylisothiazolyl-3 | |
| 340 | H | H | NO₂ | H | 4-methylisothiazolyl-3 | |
| 341 | H | H | NO₂ | H | 5-methyl-1,2,3-thiadiazolyl-4 | |
| 342 | H | H | NO₂ | H | 4-methyl-1,2,3-thiadiazolyl-5 | 145–147 |
| 343 | H | H | NO₂ | H | pyrryl-1 | |
| 344 | H | H | NO₂ | H | imidazolyl-1 | |
| 345 | H | H | NO₂ | H | pyrazolyl-1 | |
| 346 | H | H | NO₂ | H | 1,3,4-triazolyl-1 | |
| 347 | H | H | NO₂ | H | 1,2,4-triazolyl-1 | |
| 348 | H | H | NO₂ | Cl | thenyl-2 | |
| 349 | H | H | NO₂ | Cl | thenyl-3 | |
| 350 | H | H | NO₂ | Cl | 2-chlorothenyl-3 | |
| 351 | H | H | NO₂ | Cl | 5-chlorothenyl-2 | |
| 352 | H | H | NO₂ | Cl | 5-nitrothenyl-2 | |
| 353 | H | H | NO₂ | Cl | 4-methylthenyl-2 | |
| 354 | H | H | NO₂ | Cl | 3-methylthenyl-2 | |
| 355 | H | H | NO₂ | Cl | 2-methylthenyl-3 | |
| 356 | H | H | NO₂ | Cl | 3-methylthenyl-4 | |
| 357 | H | H | NO₂ | Cl | 2,5-dimethylthenyl-4 | |
| 358 | H | H | NO₂ | Cl | 2,3-dichlorothenyl-4 | |
| 359 | H | H | NO₂ | Cl | 5-methylthenyl-2 | |
| 360 | H | H | NO₂ | Cl | pyrryl-2 | |
| 361 | H | H | NO₂ | Cl | pyrryl-3 | |
| 362 | H | H | NO₂ | Cl | 3-methylpyrryl-2 | |
| 363 | H | H | NO₂ | Cl | 2-methylpyrryl-3 | |
| 364 | H | H | NO₂ | Cl | 5-chloropyrryl-2 | |
| 365 | H | H | NO₂ | Cl | oxazolyl-2 | |
| 366 | H | H | NO₂ | Cl | oxazolyl-4 | |
| 367 | H | H | NO₂ | Cl | oxazolyl-5 | |
| 368 | H | H | NO₂ | Cl | 1,2,3-thiadiazolyl-4 | 205–207 |
| 369 | H | H | NO₂ | Cl | 4-methyloxazolyl-5 | |
| 370 | H | H | NO₂ | Cl | 2-methyloxazolyl-5 | |
| 371 | H | H | NO₂ | Cl | thiazolyl-2 | |
| 372 | H | H | NO₂ | Cl | thiazolyl-4 | |
| 373 | H | H | NO₂ | Cl | thiazolyl-5 | |
| 374 | H | H | NO₂ | Cl | 4-methylthiazolyl-5 | |
| 375 | H | H | NO₂ | Cl | 2-methylthiazolyl-5 | |
| 376 | H | H | NO₂ | Cl | imidazolyl-4 | |
| 377 | H | H | NO₂ | Cl | imidazolyl-5 | |
| 378 | H | H | NO₂ | Cl | 4-methylimidazolyl-5 | |
| 379 | H | H | NO₂ | Cl | 1-methylimidazolyl-5 | |
| 380 | H | H | NO₂ | Cl | 4-nitroimidazolyl-1 | |
| 381 | H | H | NO₂ | Cl | 2-methyl-4-nitroimidazolyl-1 | |
| 382 | H | H | NO₂ | Cl | 4,5-dichloroimidazolyl-1 | |
| 383 | H | H | NO₂ | Cl | 1-methylpyrryl-2 | |
| 384 | H | H | NO₂ | Cl | isoxazolyl-3 | 132–134 |
| 385 | H | H | NO₂ | Cl | isoxazolyl-4 | |

-continued

| No. | R¹ | R² | R³ | R⁴ | R⁵ | m.p. [°C.] |
|---|---|---|---|---|---|---|
| 386 | H | H | NO₂ | Cl | 5-chloromethylisoxazolyl-3 | 138–141 |
| 387 | H | H | NO₂ | Cl | isothiazolyl-3 | |
| 388 | H | H | NO₂ | Cl | isothiazolyl-4 | |
| 389 | H | H | NO₂ | Cl | isothiazolyl-5 | |
| 390 | H | H | NO₂ | Cl | 4-methylisothiazolyl-5 | |
| 391 | H | H | NO₂ | Cl | pyrazolyl-4 | |
| 392 | H | H | NO₂ | Cl | pyrazolyl-5 | |
| 393 | H | H | NO₂ | Cl | 4-chloropyrazolyl-5 | |
| 394 | H | H | NO₂ | Cl | 1-methylpyrazolyl-5 | |
| 395 | H | H | NO₂ | Cl | 1,2,3-thiadiazolyl-5 | |
| 396 | H | H | NO₂ | Cl | 1,2,3-oxadiazolyl-5 | |
| 397 | H | H | NO₂ | Cl | 1,2,3-oxadiazolyl-4 | |
| 398 | H | H | NO₂ | Cl | 5-methyl-1,2,3-oxadiazolyl-4 | |
| 399 | H | H | NO₂ | Cl | 4-methyl-1,2,3-oxadiazolyl-5 | |
| 400 | H | H | NO₂ | Cl | 1,3,4-thiadiazolyl-2 | |
| 401 | H | H | NO₂ | Cl | 2-methyl-1,3,4-thiadiazolyl-5 | |
| 402 | H | H | NO₂ | Cl | 1,2,4-thiadiazolyl-3 | |
| 403 | H | H | NO₂ | Cl | 1,2,4-thiadiazolyl-5 | |
| 404 | H | H | NO₂ | Cl | 3-methyl-1,2,4-thiadiazolyl-5 | |
| 405 | H | H | NO₂ | Cl | 1,2,4-oxadiazolyl-3 | |
| 406 | H | H | NO₂ | Cl | 1,2,4-oxadiazolyl-5 | |
| 407 | H | H | NO₂ | Cl | 1,2,4-triazolyl-5 | |
| 408 | H | H | NO₂ | Cl | 1,2,4-triazolyl-3 | |
| 409 | H | H | NO₂ | Cl | 1,3,4-oxadiazolyl-5 | |
| 410 | H | H | NO₂ | Cl | 2-methyl-1,3,4-oxadiazolyl-5 | |
| 411 | H | H | NO₂ | Cl | 2-chloro-1,3,4-oxadiazolyl-5 | |
| 412 | H | H | NO₂ | Cl | 1,2,5-oxadiazolyl-3 | |
| 413 | H | H | NO₂ | Cl | 3-methyl-1,2,5-oxadiazolyl-4 | |
| 414 | H | H | NO₂ | Cl | 1,2,5-thiadiazolyl-3 | |
| 415 | H | H | NO₂ | Cl | 3-methyl-1,2,5-thiadiazolyl-4 | |
| 416 | H | H | NO₂ | Cl | 2-methylfuryl-5 | |
| 417 | H | H | NO₂ | Cl | 2,5-dimethylfuryl | 116–118 |
| 418 | H | H | NO₂ | Cl | 2-chloro-furyl-5 | |
| 419 | H | H | NO₂ | Cl | 5-methyloxazolyl-4 | |
| 420 | H | H | NO₂ | Cl | 4-methyloxazolyl-2 | |
| 421 | H | H | NO₂ | Cl | 2-bromofuryl-5 | |
| 422 | H | H | NO₂ | Cl | 2-methylfuryl-4 | |
| 423 | H | H | NO₂ | Cl | 5-methylisoxazolyl-3 | |
| 424 | H | H | NO₂ | Cl | 4-methylisoxazolyl-3 | |
| 425 | H | H | NO₂ | Cl | 5-methylisothiazolyl-3 | |
| 426 | H | H | NO₂ | Cl | 4-methylisothiazolyl-3 | |
| 427 | H | H | NO₂ | Cl | 4-methyl-1,2,3-thiadiazolyl-5 | 230–234 |
| 428 | H | H | NO₂ | Cl | 5-methyl-1,2,3-thiadiazolyl-4 | 145–148 |
| 429 | H | H | NO₂ | Cl | pyrryl-1 | |
| 430 | H | H | NO₂ | Cl | imidazolyl-1 | |
| 431 | H | H | NO₂ | Cl | pyrazolyl-1 | |
| 432 | H | H | NO₂ | Cl | 1,3,4-triazolyl-1 | |
| 433 | H | H | NO₂ | Cl | 1,2,4-triazolyl-1 | |
| 434 | H | H | NO₂ | Br | thenyl-2 | |
| 435 | H | H | NO₂ | Br | thenyl-3 | |
| 436 | H | H | NO₂ | Br | 2-chlorothenyl-3 | |
| 437 | H | H | NO₂ | Br | 5-chlorothenyl-2 | |
| 438 | H | H | NO₂ | Br | 5-nitrothenyl-2 | |
| 439 | H | H | NO₂ | Br | 4-methylthenyl-2 | |
| 440 | H | H | NO₂ | Br | 3-methylthenyl-2 | |
| 441 | H | H | NO₂ | Br | 2-methylthenyl-3 | |
| 442 | H | H | NO₂ | Br | 3-methylthenyl-4 | |
| 443 | H | H | NO₂ | Br | 2,5-dimethylthenyl-4 | |
| 444 | H | H | NO₂ | Br | 2,3-dichlorothenyl-4 | |
| 445 | H | H | NO₂ | Br | 5-methylthenyl-2 | |
| 446 | H | H | NO₂ | Br | pyrryl-2 | |
| 447 | H | H | NO₂ | Br | pyrryl-3 | |
| 448 | H | H | NO₂ | Br | 3-methylpyrryl-2 | |
| 449 | H | H | NO₂ | Br | 2-methylpyrryl-3 | |
| 450 | H | H | NO₂ | Br | 5-chloropyrryl-2 | |
| 451 | H | H | NO₂ | Br | oxazolyl-2 | |
| 452 | H | H | NO₂ | Br | oxazolyl-4 | |
| 453 | H | H | NO₂ | Br | oxazolyl-5 | |
| 454 | H | H | NO₂ | Br | 4-methyloxazolyl-5 | |
| 455 | H | H | NO₂ | Br | 2-methyloxazolyl-5 | |
| 456 | H | H | NO₂ | Br | thiazolyl-2 | |
| 457 | H | H | NO₂ | Br | thiazolyl-4 | |
| 458 | H | H | NO₂ | Br | thiazolyl-5 | |
| 459 | H | H | NO₂ | Br | 4-methylthiazolyl-5 | |
| 460 | H | H | NO₂ | Br | 2-methylthiazolyl-5 | |
| 461 | H | H | NO₂ | Br | imidazolyl-4 | |
| 462 | H | H | NO₂ | Br | imidazolyl-5 | |
| 463 | H | H | NO₂ | Br | 4-methylimidazolyl-5 | |
| 464 | H | H | NO₂ | Br | 1-methylimidazolyl-5 | |
| 465 | H | H | NO₂ | Br | 4-nitroimidazolyl-1 | |
| 466 | H | H | NO₂ | Br | 2-methyl-4-nitroimidazolyl-1 | |

-continued

| No. | R¹ | R² | R³ | R⁴ | R⁵ | m.p. [°C.] |
|---|---|---|---|---|---|---|
| 467 | H | H | NO₂ | Br | 4,5-dichloroimidazolyl-1 | |
| 468 | H | H | NO₂ | Br | 1-methylpyrryl-2 | |
| 469 | H | H | NO₂ | Br | isoxazolyl-3 | 143–147 |
| 470 | H | H | NO₂ | Br | isoxazolyl-4 | |
| 471 | H | H | NO₂ | Br | isoxazolyl-5 | 138–141 |
| 472 | H | H | NO₂ | Br | 5-chloromethyl-isoxazolyl-3 | |
| 473 | H | H | NO₂ | Br | isothiazolyl-3 | |
| 474 | H | H | NO₂ | Br | isothiazolyl-4 | |
| 475 | H | H | NO₂ | Br | isothiazolyl-5 | |
| 476 | H | H | NO₂ | Br | 4-methylisothiazolyl-5 | |
| 477 | H | H | NO₂ | Br | pyrazolyl-4 | |
| 478 | H | H | NO₂ | Br | pyrazolyl-5 | |
| 479 | H | H | NO₂ | Br | 4-chloropyrazolyl-5 | |
| 480 | H | H | NO₂ | Br | 1-methylpyrazolyl-5 | |
| 481 | H | H | NO₂ | Br | 1,2,3-thiadiazolyl-5 | |
| 482 | H | H | NO₂ | Br | 1,2,3-oxadiazolyl-5 | |
| 483 | H | H | NO₂ | Br | 1,2,3-oxadiazolyl-4 | |
| 484 | H | H | NO₂ | Br | 5-methyl-1,2,3-oxadiazolyl-4 | |
| 485 | H | H | NO₂ | Br | 4-methyl-1,2,3-oxadiazolyl-5 | |
| 486 | H | H | NO₂ | Br | 1,3,4-thiadiazolyl-2 | |
| 487 | H | H | NO₂ | Br | 2-methyl-1,3,4-thiadiazolyl-5 | |
| 488 | H | H | NO₂ | Br | 1,2,4-thiadiazolyl-3 | |
| 489 | H | H | NO₂ | Br | 1,2,4-thiadiazolyl-5 | |
| 490 | H | H | NO₂ | Br | 3-methyl-1,2,4-thiadiazolyl-5 | |
| 491 | H | H | NO₂ | Br | 1,2,4-oxadiazolyl-3 | |
| 492 | H | H | NO₂ | Br | 1,2,4-oxadiazolyl-5 | |
| 493 | H | H | NO₂ | Br | 1,2,4-triazolyl-5 | |
| 494 | H | H | NO₂ | Br | 1,2,4-triazolyl-3 | |
| 495 | H | H | NO₂ | Br | 1,3,4-oxadiazolyl-5 | |
| 496 | H | H | NO₂ | Br | 2-methyl-1,3,4-oxadiazolyl-5 | |
| 497 | H | H | NO₂ | Br | 2-chloro-1,3,4-oxadiazolyl-5 | |
| 498 | H | H | NO₂ | Br | 1,2,5-oxadiazolyl-3 | |
| 499 | H | H | NO₂ | Br | 3-methyl-1,2,5-oxadiazolyl-4 | |
| 500 | H | H | NO₂ | Br | 1,2,5-thiadiazolyl-3 | |
| 501 | H | H | NO₂ | Br | 3-methyl-1,2,5-thiadiazolyl-4 | |
| 502 | H | H | NO₂ | Br | 2-methylfuryl-5 | |
| 503 | H | H | NO₂ | Br | 2,5-dimethylfuryl | 121–123 |
| 504 | H | H | NO₂ | Br | 2-chlorofuryl-5 | |
| 505 | H | H | NO₂ | Br | 5-methyloxazolyl-4 | |
| 506 | H | H | NO₂ | Br | 4-methyloxazolyl-2 | |
| 507 | H | H | NO₂ | Br | 2-bromofuryl-5 | |
| 508 | H | H | NO₂ | Br | 2-methylfuryl-4 | |
| 509 | H | H | NO₂ | Br | 5-methylisoxazolyl-3 | |
| 510 | H | H | NO₂ | Br | 4-methylisoxazolyl-3 | |
| 511 | H | H | NO₂ | Br | 5-methylisothiazolyl-3 | |
| 512 | H | H | NO₂ | Br | 4-methylisothiazolyl-3 | |
| 513 | H | H | NO₂ | Br | 4-methyl-1,2,3-thiadiazolyl-5 | |
| 514 | H | H | NO₂ | Br | 5-methyl-1,2,3-thiadiazolyl-4 | |
| 515 | H | H | NO₂ | Br | pyrryl-1 | |
| 516 | H | H | NO₂ | Br | imidazolyl-1 | |
| 517 | H | H | NO₂ | Br | pyrazolyl-1 | |
| 518 | H | H | NO₂ | Br | 1,3,4-triazolyl-1 | |
| 519 | H | H | NO₂ | Br | 1,2,4-triazolyl-1 | |
| 520 | H | H | NO₂ | I | thenyl-2 | |
| 521 | H | H | NO₂ | I | thenyl-3 | |
| 522 | H | H | NO₂ | I | 2-chlorothenyl-3 | |
| 523 | H | H | NO₂ | I | 5-chlorothenyl-2 | |
| 524 | H | H | NO₂ | I | 5-nitrothenyl-2 | |
| 525 | H | H | NO₂ | I | 4-methylthenyl-2 | |
| 526 | H | H | NO₂ | I | 3-methylthenyl-2 | |
| 527 | H | H | NO₂ | I | 2-methylthenyl-3 | |
| 528 | H | H | NO₂ | I | 3-methylthenyl-4 | |
| 529 | H | H | NO₂ | I | 2,5-dimethylthenyl-4 | |
| 530 | H | H | NO₂ | I | 2,3-dichlorothenyl-4 | |
| 531 | H | H | NO₂ | I | 5-methylthenyl-2 | |
| 532 | H | H | NO₂ | I | pyrryl-2 | |
| 533 | H | H | NO₂ | I | pyrryl-3 | |
| 534 | H | H | NO₂ | I | 3-methylpyrryl-2 | |
| 535 | H | H | NO₂ | I | 2-methylpyrryl-3 | |
| 536 | H | H | NO₂ | I | 5-chloropyrryl-2 | |
| 537 | H | H | NO₂ | I | oxazolyl-2 | |
| 538 | H | H | NO₂ | I | oxazolyl-4 | |
| 539 | H | H | NO₂ | I | oxazolyl-5 | |
| 540 | H | H | NO₂ | I | 1,2,3-thiadiazolyl-4 | |
| 541 | H | H | NO₂ | I | 4-methyloxazolyl-5 | |
| 542 | H | H | NO₂ | I | 2-methyloxazolyl-5 | |
| 543 | H | H | NO₂ | I | thiazolyl-2 | |
| 544 | H | H | NO₂ | I | thiazolyl-4 | |
| 545 | H | H | NO₂ | I | thiazolyl-5 | |
| 546 | H | H | NO₂ | I | 4-methylthiazolyl-5 | |
| 547 | H | H | NO₂ | I | 2-methylthiazolyl-5 | |

-continued

| No. | R¹ | R² | R³ | R⁴ | R⁵ | m.p. [°C.] |
|---|---|---|---|---|---|---|
| 548 | H | H | NO₂ | I | imidazolyl-4 | |
| 549 | H | H | NO₂ | I | imidazolyl-5 | |
| 550 | H | H | NO₂ | I | 4-methylimidazolyl-5 | |
| 551 | H | H | NO₂ | I | 1-methylimidazolyl-5 | |
| 552 | H | H | NO₂ | I | 4-nitroimidazolyl-1 | |
| 553 | H | H | NO₂ | I | 2-methyl-4-nitroimidazolyl-1 | |
| 554 | H | H | NO₂ | I | 4,5-dichloroimidazolyl-1 | |
| 555 | H | H | NO₂ | I | 1-methylpyrryl-2 | |
| 556 | H | H | NO₂ | I | isoxazolyl-3 | |
| 557 | H | H | NO₂ | I | isoxazolyl-4 | |
| 558 | H | H | NO₂ | I | isoxazolyl-5 | |
| 559 | H | H | NO₂ | I | 5-chloromethylisoxazolyl-3 | |
| 560 | H | H | NO₂ | I | isothiazolyl-3 | |
| 561 | H | H | NO₂ | I | isothiazolyl-4 | |
| 562 | H | H | NO₂ | I | isothiazolyl-5 | |
| 563 | H | H | NO₂ | I | 4-methylisothiazolyl-5 | |
| 564 | H | H | NO₂ | I | pyrazolyl-4 | |
| 565 | H | H | NO₂ | I | pyrazolyl-5 | |
| 566 | H | H | NO₂ | I | 4-chloropyrazolyl-5 | |
| 567 | H | H | NO₂ | I | 1-methylpyrazolyl-5 | |
| 568 | H | H | NO₂ | I | 1,2,3-thiadiazolyl-5 | |
| 569 | H | H | NO₂ | I | 1,2,3-oxadiazolyl-5 | |
| 570 | H | H | NO₂ | I | 1,2,3-oxadiazolyl-4 | |
| 571 | H | H | NO₂ | I | 5-methyl-1,2,3-oxadiazolyl-4 | |
| 572 | H | H | NO₂ | I | 4-methyl-1,2,3-oxadiazolyl-5 | |
| 573 | H | H | NO₂ | I | 1,3,4-thiadiazolyl-2 | |
| 574 | H | H | NO₂ | I | 2-methyl-1,3,4-thiadiazolyl-5 | |
| 575 | H | H | NO₂ | I | 1,2,4-thiadiazolyl-3 | |
| 576 | H | H | NO₂ | I | 1,2,4-thiadiazolyl-5 | |
| 577 | H | H | NO₂ | I | 3-methyl-1,2,4-thiadiazolyl-5 | |
| 578 | H | H | NO₂ | I | 1,2,4-oxadiazolyl-3 | |
| 579 | H | H | NO₂ | I | 1,2,4-oxadiazolyl-5 | |
| 580 | H | H | NO₂ | I | 1,2,4-triazolyl-5 | |
| 581 | H | H | NO₂ | I | 1,2,4-triazolyl-3 | |
| 582 | H | H | NO₂ | I | 1,3,4-oxadiazolyl-5 | |
| 583 | H | H | NO₂ | I | 2-methyl-1,3,4-oxadiazolyl-5 | |
| 584 | H | H | NO₂ | I | 2-chloro-1,3,4-oxadiazolyl-5 | |
| 585 | H | H | NO₂ | I | 1,2,5-oxadiazolyl-3 | |
| 586 | H | H | NO₂ | I | 3-methyl-1,2,5-oxadiazolyl-4 | |
| 587 | H | H | NO₂ | I | 1,2,5-thiadiazolyl-3 | |
| 588 | H | H | NO₂ | I | 3-methyl-1,2,5-thiadiazolyl-4 | |
| 589 | H | H | NO₂ | I | 2-methylfuryl-5 | |
| 590 | H | H | NO₂ | I | 2,5-dimethylfuryl-4 | |
| 591 | H | H | NO₂ | I | 2-chlorofuryl-5 | |
| 592 | H | H | NO₂ | I | 5-methyloxazolyl-4 | |
| 593 | H | H | NO₂ | I | 4-methyloxazolyl-2 | |
| 594 | H | H | NO₂ | I | 2-bromofuryl-5 | |
| 595 | H | H | NO₂ | I | 2-methylfuryl-4 | |
| 596 | H | H | NO₂ | I | 5-methylisoxazolyl-3 | |
| 597 | H | H | NO₂ | I | 4-methylisoxazolyl-3 | |
| 598 | H | H | NO₂ | I | 5-methylisothiazolyl-3 | |
| 599 | H | H | NO₂ | I | 4-methylisothiazolyl-3 | |
| 600 | H | H | NO₂ | I | 4-methyl-1,2,3-thiadiazolyl-5 | |
| 601 | H | H | NO₂ | I | 5-methyl-1,2,3-thiadiazolyl-4 | |
| 602 | H | H | NO₂ | I | pyrryl-1 | |
| 603 | H | H | NO₂ | I | imidazolyl-1 | |
| 604 | H | H | NO₂ | I | pyrazolyl-1 | |
| 605 | H | H | NO₂ | I | 1,3,4-triazolyl-1 | |
| 606 | H | H | NO₂ | I | 1,2,4-triazolyl-1 | |
| 607 | H | H | NO₂ | NO₂ | thenyl-2 | |
| 608 | H | H | NO₂ | NO₂ | thenyl-3 | |
| 609 | H | H | NO₂ | NO₂ | 2-chlorothenyl-3 | |
| 610 | H | H | NO₂ | NO₂ | 5-chlorothenyl-2 | |
| 611 | H | H | NO₂ | NO₂ | 5-nitrothenyl-2 | |
| 612 | H | H | NO₂ | NO₂ | 4-methylthenyl-2 | |
| 613 | H | H | NO₂ | NO₂ | 3-methylthenyl-2 | |
| 614 | H | H | NO₂ | NO₂ | 2-methylthenyl-3 | |
| 615 | H | H | NO₂ | NO₂ | 3-methylthenyl-4 | |
| 616 | H | H | NO₂ | NO₂ | 2,5-dimethylthenyl-4 | |
| 617 | H | H | NO₂ | NO₂ | 2,3-dichlorothenyl-4 | |
| 618 | H | H | NO₂ | NO₂ | 5-methylthenyl-2 | |
| 619 | H | H | NO₂ | NO₂ | pyrryl-2 | |
| 620 | H | H | NO₂ | NO₂ | pyrryl-3 | |
| 621 | H | H | NO₂ | NO₂ | 3-methylpyrryl-2 | |
| 622 | H | H | NO₂ | NO₂ | 2-methylpyrryl-3 | |
| 623 | H | H | NO₂ | NO₂ | 5-chloropyrryl-2 | |
| 624 | H | H | NO₂ | NO₂ | oxazolyl-2 | |
| 625 | H | H | NO₂ | NO₂ | oxazolyl-4 | |
| 626 | H | H | NO₂ | NO₂ | oxazolyl-5 | |
| 627 | H | H | NO₂ | NO₂ | 1,2,3-thiadiazolyl-4 | 172–174 |
| 628 | H | H | NO₂ | NO₂ | 4-methyloxazolyl-5 | |

-continued

| No. | R¹ | R² | R³ | R⁴ | R⁵ | m.p. [°C.] |
|---|---|---|---|---|---|---|
| 629 | H | H | $NO_2$ | $NO_2$ | 2-methyloxazolyl-5 | |
| 630 | H | H | $NO_2$ | $NO_2$ | thiazolyl-2 | |
| 631 | H | H | $NO_2$ | $NO_2$ | thiazolyl-4 | |
| 632 | H | H | $NO_2$ | $NO_2$ | thiazolyl-5 | |
| 633 | H | H | $NO_2$ | $NO_2$ | 4-methylthiazolyl-5 | |
| 634 | H | H | $NO_2$ | $NO_2$ | 2-methylthiazolyl-5 | |
| 635 | H | H | $NO_2$ | $NO_2$ | imidazolyl-4 | |
| 636 | H | H | $NO_2$ | $NO_2$ | imidazolyl-5 | |
| 637 | H | H | $NO_2$ | $NO_2$ | 4-methylimidazolyl-5 | |
| 638 | H | H | $NO_2$ | $NO_2$ | 1-methylimidazolyl-5 | |
| 639 | H | H | $NO_2$ | $NO_2$ | 4-nitroimidazolyl-1 | |
| 640 | H | H | $NO_2$ | $NO_2$ | 2-methyl-4-nitroimidazolyl-1 | |
| 641 | H | H | $NO_2$ | $NO_2$ | 4,5-dichloroimidazolyl-1 | |
| 642 | H | H | $NO_2$ | $NO_2$ | 1-methylpyrryl-2 | |
| 643 | H | H | $NO_2$ | $NO_2$ | isoxazolyl-3 | 171–174 |
| 644 | H | H | $NO_2$ | $NO_2$ | isoxazolyl-4 | |
| 645 | H | H | $NO_2$ | $NO_2$ | isoxazolyl-5 | |
| 646 | H | H | $NO_2$ | $NO_2$ | 5-chloromethylisoxazolyl-3 | |
| 647 | H | H | $NO_2$ | $NO_2$ | isothiazolyl-3 | |
| 648 | H | H | $NO_2$ | $NO_2$ | isothiazolyl-4 | |
| 649 | H | H | $NO_2$ | $NO_2$ | isothiazolyl-5 | |
| 650 | H | H | $NO_2$ | $NO_2$ | 4-methylisothiazolyl-5 | |
| 651 | H | H | $NO_2$ | $NO_2$ | pyrazolyl-4 | |
| 652 | H | H | $NO_2$ | $NO_2$ | pyrazolyl-5 | |
| 653 | H | H | $NO_2$ | $NO_2$ | 4-chloropyrazolyl-5 | |
| 654 | H | H | $NO_2$ | $NO_2$ | 1-methylpyrazolyl-5 | |
| 655 | H | H | $NO_2$ | $NO_2$ | 1,2,3-thiadiazolyl-5 | |
| 656 | H | H | $NO_2$ | $NO_2$ | 1,2,3-oxadiazolyl-5 | |
| 657 | H | H | $NO_2$ | $NO_2$ | 1,2,3-oxadiazolyl-4 | |
| 658 | H | H | $NO_2$ | $NO_2$ | 5-methyl-1,2,3-oxadiazolyl-4 | |
| 659 | H | H | $NO_2$ | $NO_2$ | 4-methyl-1,2,3-oxadiazolyl-5 | |
| 660 | H | H | $NO_2$ | $NO_2$ | 1,3,4-thiadiazolyl-2 | |
| 661 | H | H | $NO_2$ | $NO_2$ | 2-methyl-1,3,4-thiadiazolyl-5 | |
| 662 | H | H | $NO_2$ | $NO_2$ | 1,2,4-thiadiazolyl-3 | |
| 663 | H | H | $NO_2$ | $NO_2$ | 1,2,4-thiadiazolyl-5 | |
| 664 | H | H | $NO_2$ | $NO_2$ | 3-methyl-1,2,4-thiadiazolyl-5 | |
| 665 | H | H | $NO_2$ | $NO_2$ | 1,2,4-oxadiazolyl-3 | |
| 666 | H | H | $NO_2$ | $NO_2$ | 1,2,4-oxadiazolyl-5 | |
| 667 | H | H | $NO_2$ | $NO_2$ | 1,2,4-triazolyl-5 | |
| 668 | H | H | $NO_2$ | $NO_2$ | 1,2,4-triazolyl-3 | |
| 669 | H | H | $NO_2$ | $NO_2$ | 1,3,4-oxadiazolyl-5 | |
| 670 | H | H | $NO_2$ | $NO_2$ | 2-methyl-1,3,4-oxadiazolyl-5 | |
| 671 | H | H | $NO_2$ | $NO_2$ | 2-chloro-1,3,4-oxadiazolyl-5 | |
| 672 | H | H | $NO_2$ | $NO_2$ | 1,2,5-oxadiazolyl-3 | |
| 673 | H | H | $NO_2$ | $NO_2$ | 3-methyl-1,2,5-oxadiazolyl-4 | |
| 674 | H | H | $NO_2$ | $NO_2$ | 1,2,5-thiadiazolyl-3 | |
| 675 | H | H | $NO_2$ | $NO_2$ | 3-methyl-1,2,5-thiadiazolyl-4 | |
| 676 | H | H | $NO_2$ | $NO_2$ | 2-methylfuryl-5 | |
| 677 | H | H | $NO_2$ | $NO_2$ | 2,5-dimethylfuryl | 145–150 |
| 678 | H | H | $NO_2$ | $NO_2$ | 2-chlorofuryl-5 | |
| 679 | H | H | $NO_2$ | $NO_2$ | 5-methyloxazolyl-4 | |
| 680 | H | H | $NO_2$ | $NO_2$ | 4-methyloxazolyl-2 | |
| 681 | H | H | $NO_2$ | $NO_2$ | 2-bromofuryl-5 | |
| 682 | H | H | $NO_2$ | $NO_2$ | 2-methylfuryl-4 | |
| 683 | H | H | $NO_2$ | $NO_2$ | 5-methylisoxazolyl-3 | |
| 684 | H | H | $NO_2$ | $NO_2$ | 4-methylisoxazolyl-3 | |
| 685 | H | H | $NO_2$ | $NO_2$ | 5-methylisothiazolyl-3 | |
| 686 | H | H | $NO_2$ | $NO_2$ | 4-methylisothiazolyl-3 | |
| 687 | H | H | $NO_2$ | $NO_2$ | 4-methyl-1,2,3-thiadiazolyl-5 | |
| 688 | H | H | $NO_2$ | $NO_2$ | 5-methyl-1,2,3-thiadiazolyl-4 | |
| 689 | H | H | $NO_2$ | $NO_2$ | pyrryl-1 | |
| 690 | H | H | $NO_2$ | $NO_2$ | imidazolyl-1 | |
| 691 | H | H | $NO_2$ | $NO_2$ | pyrazolyl-1 | |
| 692 | H | H | $NO_2$ | $NO_2$ | 1,3,4-triazolyl-1 | |
| 693 | H | H | $NO_2$ | $NO_2$ | 1,2,4-triazolyl-1 | |
| 694 | H | H | Cl | H | thenyl-2 | |
| 695 | H | H | Cl | H | thenyl-3 | |
| 696 | H | H | Cl | H | 2-chlorothenyl-3 | |
| 697 | H | H | Cl | H | 5-chlorothenyl-2 | |
| 698 | H | H | Cl | H | 5-nitrothenyl-2 | |
| 699 | H | H | Cl | H | 4-methylthenyl-2 | |
| 700 | H | H | Cl | H | 3-methylthenyl-2 | |
| 701 | H | H | Cl | H | 2-methylthenyl-3 | |
| 702 | H | H | Cl | H | 3-methylthenyl-4 | |
| 703 | H | H | Cl | H | 2,5-dimethylthenyl-4 | |
| 704 | H | H | Cl | H | 2,3-dichlorothenyl-4 | |
| 705 | H | H | Cl | H | 5-methylthenyl-2 | |
| 706 | H | H | Cl | H | pyrryl-2 | |
| 707 | H | H | Cl | H | pyrryl-3 | |
| 708 | H | H | Cl | H | 3-methylpyrryl-2 | |
| 709 | H | H | Cl | H | 2-methylpyrryl-3 | |

-continued

| No. | R¹ | R² | R³ | R⁴ | R⁵ | m.p. [°C.] |
|---|---|---|---|---|---|---|
| 710 | H | H | Cl | H | 5-chloropyrryl-2 | |
| 711 | H | H | Cl | H | oxazolyl-2 | |
| 712 | H | H | Cl | H | oxazolyl-4 | |
| 713 | H | H | Cl | H | oxazolyl-5 | |
| 714 | H | H | Cl | H | 4-methyloxazolyl-5 | |
| 715 | H | H | Cl | H | 2-methyloxazolyl-5 | |
| 716 | H | H | Cl | H | thiazolyl-2 | |
| 717 | H | H | Cl | H | thiazolyl-4 | |
| 718 | H | H | Cl | H | thiazolyl-5 | |
| 719 | H | H | Cl | H | 4-methylthiazolyl-5 | |
| 720 | H | H | Cl | H | 2-methylthiazolyl-5 | |
| 721 | H | H | Cl | H | imidazolyl-4 | |
| 722 | H | H | Cl | H | imidazolyl-5 | |
| 723 | H | H | Cl | H | 4-methylimidazolyl-5 | |
| 724 | H | H | Cl | H | 1-methylimidazolyl-5 | |
| 725 | H | H | Cl | H | 4-nitroimidazolyl-1 | |
| 726 | H | H | Cl | H | 2-methyl-4-nitroimidazolyl-1 | |
| 727 | H | H | Cl | H | 4,5-dichloroimidazolyl-1 | |
| 728 | H | H | Cl | H | 1-methylpyrryl-2 | |
| 729 | H | H | Cl | H | isoxazolyl-3 | 135–137 |
| 730 | H | H | Cl | H | isoxazolyl-4 | |
| 731 | H | H | Cl | H | isoxazolyl-5 | 125–128 |
| 732 | H | H | Cl | H | 5-chloromethylisoxazolyl-3 | 130–133 |
| 733 | H | H | Cl | H | isothiazolyl-3 | |
| 734 | H | H | Cl | H | isothiazolyl-4 | |
| 735 | H | H | Cl | H | isothiazolyl-5 | |
| 736 | H | H | Cl | H | 4-methylisothiazolyl-5 | |
| 737 | H | H | Cl | H | pyrazolyl-4 | |
| 738 | H | H | Cl | H | pyrazolyl-5 | |
| 739 | H | H | Cl | H | 4-chloropyrazolyl-5 | |
| 740 | H | H | Cl | H | 1-methylpyrazolyl-5 | |
| 741 | H | H | Cl | H | 1,2,3-thiadiazolyl-5 | |
| 742 | H | H | Cl | H | 1,2,3-oxadiazolyl-5 | |
| 743 | H | H | Cl | H | 1,2,3-oxadiazolyl-4 | |
| 744 | H | H | Cl | H | 5-methyl-1,2,3-oxadiazolyl-4 | |
| 745 | H | H | Cl | H | 4-methyl-1,2,3-oxadiazolyl-5 | |
| 746 | H | H | Cl | H | 1,3,4-thiadiazolyl-2 | |
| 747 | H | H | Cl | H | 2-methyl-1,3,4-thiadiazolyl-5 | |
| 748 | H | H | Cl | H | 1,2,4-thiadiazolyl-3 | |
| 749 | H | H | Cl | H | 1,2,4-thiadiazolyl-5 | |
| 750 | H | H | Cl | H | 3-methyl-1,2,4-thiadiazolyl-5 | |
| 751 | H | H | Cl | H | 1,2,4-oxadiazolyl-3 | |
| 752 | H | H | Cl | H | 1,2,4-oxadiazolyl-5 | |
| 753 | H | H | Cl | H | 1,2,4-triazolyl-5 | |
| 754 | H | H | Cl | H | 1,2,4-triazolyl-3 | |
| 755 | H | H | Cl | H | 1,3,4-oxadiazolyl-5 | |
| 756 | H | H | Cl | H | 2-methyl-1,3,4-oxadiazolyl-5 | |
| 757 | H | H | Cl | H | 2-chloro-1,3,4-oxadiazolyl-5 | |
| 758 | H | H | Cl | H | 1,2,5-oxadiazolyl-3 | |
| 759 | H | H | Cl | H | 3-methyl-1,2,5-oxadiazolyl-4 | |
| 760 | H | H | Cl | H | 1,2,5-thiadiazolyl-3 | |
| 761 | H | H | Cl | H | 3-methyl-1,2,5-thiadiazolyl-4 | |
| 762 | H | H | Cl | H | 2-methylfuryl-5 | |
| 763 | H | H | Cl | H | 2,5-dimethylfuryl-4 | 105–106 |
| 764 | H | H | Cl | H | 2-chloro-furyl-5 | |
| 765 | H | H | Cl | H | 5-methyloxazolyl-4 | |
| 766 | H | H | Cl | H | 4-methyloxazolyl-2 | |
| 767 | H | H | Cl | H | 2-bromofuryl-5 | |
| 768 | H | H | Cl | H | 2-methylfuryl-4 | |
| 769 | H | H | Cl | H | 5-methylisoxazolyl-3 | |
| 770 | H | H | Cl | H | 4-methylisoxazolyl-3 | |
| 771 | H | H | Cl | H | 5-methylisothiazolyl-3 | |
| 772 | H | H | Cl | H | 4-methylisothiazolyl-3 | |
| 773 | H | H | Cl | H | 5-methyl-1,2,3-thiadiazolyl-4 | |
| 774 | H | H | Cl | H | pyrryl-1 | |
| 775 | H | H | Cl | H | imidazolyl-1 | |
| 776 | H | H | Cl | H | pyrazolyl-1 | |
| 777 | H | H | Cl | H | 1,3,4-triazolyl-1 | |
| 778 | H | H | Cl | H | 1,2,4-triazolyl-1 | |
| 779 | H | H | Cl | NO₂ | thenyl-2 | |
| 780 | H | H | Cl | NO₂ | thenyl-3 | |
| 781 | H | H | Cl | NO₂ | 2-chlorothenyl-3 | |
| 782 | H | H | Cl | NO₂ | 5-chlorothenyl-2 | |
| 783 | H | H | Cl | NO₂ | 5-nitrothenyl-2 | |
| 784 | H | H | Cl | NO₂ | 4-methylthenyl-2 | |
| 785 | H | H | Cl | NO₂ | 3-methylthenyl-2 | |
| 786 | H | H | Cl | NO₂ | 2-methylthenyl-3 | |
| 787 | H | H | Cl | NO₂ | 3-methylthenyl-4 | |
| 788 | H | H | Cl | NO₂ | 2,5-dimethylthenyl-4 | |
| 789 | H | H | Cl | NO₂ | 2,3-dichlorothenyl-4 | |
| 790 | H | H | Cl | NO₂ | 5-methylthenyl-2 | |

-continued

| No. | R¹ | R² | R³ | R⁴ | R⁵ | m.p. [°C] |
|---|---|---|---|---|---|---|
| 791 | H | H | Cl | NO₂ | pyrryl-2 | |
| 792 | H | H | Cl | NO₂ | pyrryl-3 | |
| 793 | H | H | Cl | NO₂ | 3-methylpyrryl-2 | |
| 794 | H | H | Cl | NO₂ | 2-methylpyrryl-3 | |
| 795 | H | H | Cl | NO₂ | 5-chloropyrryl-2 | |
| 796 | H | H | Cl | NO₂ | oxazolyl-2 | |
| 797 | H | H | Cl | NO₂ | oxazolyl-4 | |
| 798 | H | H | Cl | NO₂ | oxazolyl-5 | |
| 799 | H | H | Cl | NO₂ | 1,2,3-thiadiazolyl-4 | |
| 800 | H | H | Cl | NO₂ | 4-methyloxazolyl-5 | |
| 801 | H | H | Cl | NO₂ | 2-methyloxazolyl-5 | |
| 802 | H | H | Cl | NO₂ | thiazolyl-2 | |
| 803 | H | H | Cl | NO₂ | thiazolyl-4 | |
| 804 | H | H | Cl | NO₂ | thiazolyl-5 | |
| 805 | H | H | Cl | NO₂ | 4-methylthiazolyl-5 | |
| 806 | H | H | Cl | NO₂ | 2-methylthiazolyl-5 | |
| 807 | H | H | Cl | NO₂ | imidazolyl-4 | |
| 808 | H | H | Cl | NO₂ | imidazolyl-5 | |
| 809 | H | H | Cl | NO₂ | 4-methylimidazolyl-5 | |
| 810 | H | H | Cl | NO₂ | 1-methylimidazolyl-5 | |
| 811 | H | H | Cl | NO₂ | 4-nitroimidazolyl-5 | |
| 812 | H | H | Cl | NO₂ | 2-methyl-4-nitroimidazolyl-1 | |
| 813 | H | H | Cl | NO₂ | 4,5-dichloroimidazolyl-1 | |
| 814 | H | H | Cl | NO₂ | 1-methylpyrryl-2 | |
| 815 | H | H | Cl | NO₂ | isoxazolyl-3 | 128–130 |
| 816 | H | H | Cl | NO₂ | isoxazolyl-4 | |
| 817 | H | H | Cl | NO₂ | isoxazolyl-5 | |
| 818 | H | H | Cl | NO₂ | 5-chloromethylisoxazolyl-3 | 122–125 |
| 819 | H | H | Cl | NO₂ | isothiazolyl-3 | |
| 820 | H | H | Cl | NO₂ | isothiazolyl-4 | |
| 821 | H | H | Cl | NO₂ | isothiazolyl-5 | |
| 822 | H | H | Cl | NO₂ | 4-methylisothiazolyl-5 | |
| 823 | H | H | Cl | NO₂ | pyrazolyl-4 | |
| 824 | H | H | Cl | NO₂ | pyrazolyl-5 | |
| 825 | H | H | Cl | NO₂ | 4-chloropyrazolyl-5 | |
| 826 | H | H | Cl | NO₂ | 1-methylpyrazolyl-5 | |
| 827 | H | H | Cl | NO₂ | 1,2,3-thiadiazolyl-5 | |
| 828 | H | H | Cl | NO₂ | 1,2,3-oxadiazolyl-5 | |
| 829 | H | H | Cl | NO₂ | 1,2,3-oxadiazolyl-4 | |
| 830 | H | H | Cl | NO₂ | 5-methyl-1,2,3-oxadiazolyl-4 | |
| 831 | H | H | Cl | NO₂ | 4-methyl-1,2,3-oxadiazolyl-5 | |
| 832 | H | H | Cl | NO₂ | 1,3,4-thiadiazolyl-2 | |
| 833 | H | H | Cl | NO₂ | 2-methyl-1,3,4-thiadiazolyl-5 | |
| 834 | H | H | Cl | NO₂ | 1,2,4-thiadiazolyl-3 | |
| 835 | H | H | Cl | NO₂ | 1,2,4-thiadiazolyl-5 | |
| 836 | H | H | Cl | NO₂ | 3-methyl-1,2,4-thiadiazolyl-5 | |
| 837 | H | H | Cl | NO₂ | 1,2,4-oxadiazolyl-3 | |
| 838 | H | H | Cl | NO₂ | 1,2,4-oxadiazolyl-5 | |
| 839 | H | H | Cl | NO₂ | 1,2,4-triazolyl-5 | |
| 840 | H | H | Cl | NO₂ | 1,2,4-triazolyl-3 | |
| 841 | H | H | Cl | NO₂ | 1,3,4-oxadiazolyl-5 | |
| 842 | H | H | Cl | NO₂ | 2-methyl-1,3,4-oxadiazolyl-5 | |
| 843 | H | H | Cl | NO₂ | 2-chloro-1,3,4-oxadiazolyl-5 | |
| 844 | H | H | Cl | NO₂ | 1,2,5-oxadiazolyl-3 | |
| 845 | H | H | Cl | NO₂ | 3-methyl-1,2,5-oxadiazolyl-4 | |
| 846 | H | H | Cl | NO₂ | 1,2,5-thiadiazolyl-3 | |
| 847 | H | H | Cl | NO₂ | 3-methyl-1,2,5-thiadiazolyl-4 | |
| 848 | H | H | Cl | NO₂ | 2-methylfuryl-5 | |
| 849 | H | H | Cl | NO₂ | 2,5-dimethylfuryl-4 | 141–144 |
| 850 | H | H | Cl | NO₂ | 2-chlorofuryl-5 | |
| 851 | H | H | Cl | NO₂ | 5-methyloxazolyl-4 | |
| 852 | H | H | Cl | NO₂ | 4-methyloxazolyl-2 | |
| 853 | H | H | Cl | NO₂ | 2-bromofuryl-5 | |
| 854 | H | H | Cl | NO₂ | 2-methylfuryl-4 | |
| 855 | H | H | Cl | NO₂ | 5-methylisoxazolyl-3 | |
| 856 | H | H | Cl | NO₂ | 4-methylisoxazolyl-3 | |
| 857 | H | H | Cl | NO₂ | 5-methylisothiazolyl-3 | |
| 858 | H | H | Cl | NO₂ | 4-methylisothiazolyl-3 | |
| 859 | H | H | Cl | NO₂ | 4-methyl-1,2,3-thiadiazolyl-5 | 137–138 |
| 860 | H | H | Cl | NO₂ | 5-methyl-1,2,3-thiadiazolyl-4 | |
| 861 | H | H | Cl | NO₂ | pyrryl-1 | |
| 862 | H | H | Cl | NO₂ | imidazolyl-1 | |
| 863 | H | H | Cl | NO₂ | pyrazolyl-1 | |
| 864 | H | H | Cl | NO₂ | 1,3,4-triazolyl-1 | |
| 865 | H | H | Cl | NO₂ | 1,2,4-triazolyl-1 | |
| 866 | H | H | Br | NO₂ | thenyl-2 | |
| 867 | H | H | Br | NO₂ | thenyl-3 | |
| 868 | H | H | Br | NO₂ | 2-chlorothenyl-3 | |
| 869 | H | H | Br | NO₂ | 5-chlorothenyl-2 | |
| 870 | H | H | Br | NO₂ | 5-nitrothenyl-2 | |
| 871 | H | H | Br | NO₂ | 4-methylthenyl-2 | |

-continued

| No. | R¹ | R² | R³ | R⁴ | R⁵ | m.p. [°C.] |
|---|---|---|---|---|---|---|
| 872 | H | H | Br | NO₂ | 3-methylthenyl-2 | |
| 873 | H | H | Br | NO₂ | 2-methylthenyl-3 | |
| 874 | H | H | Br | NO₂ | 3-methylthenyl-4 | |
| 875 | H | H | Br | NO₂ | 2,5-dimethylthenyl-4 | |
| 876 | H | H | Br | NO₂ | 2,3-dichlorothenyl-4 | |
| 877 | H | H | Br | NO₂ | 5-methylthenyl-2 | |
| 878 | H | H | Br | NO₂ | pyrryl-2 | |
| 879 | H | H | Br | NO₂ | pyrryl-3 | |
| 880 | H | H | Br | NO₂ | 3-methylpyrryl-2 | |
| 881 | H | H | Br | NO₂ | 2-methylpyrryl-3 | |
| 882 | H | H | Br | NO₂ | 5-chloropyrryl-2 | |
| 883 | H | H | Br | NO₂ | oxazolyl-2 | |
| 884 | H | H | Br | NO₂ | oxazolyl-4 | |
| 885 | H | H | Br | NO₂ | oxazolyl-5 | |
| 886 | H | H | Br | NO₂ | 1,2,3-thiadiazolyl | 172 (decomp.) |
| 887 | H | H | Br | NO₂ | 4-methyloxazolyl-5 | |
| 888 | H | H | Br | NO₂ | 2-methyloxazolyl-5 | |
| 889 | H | H | Br | NO₂ | thiazolyl-2 | |
| 890 | H | H | Br | NO₂ | thiazolyl-4 | |
| 891 | H | H | Br | NO₂ | thiazolyl-5 | |
| 892 | H | H | Br | NO₂ | 4-methylthiazolyl-5 | |
| 893 | H | H | Br | NO₂ | 2-methylthiazolyl-5 | |
| 894 | H | H | Br | NO₂ | imidazolyl-4 | |
| 895 | H | H | Br | NO₂ | imidazolyl-5 | |
| 896 | H | H | Br | NO₂ | 4-methylimidazolyl-5 | |
| 897 | H | H | Br | NO₂ | 1-methylimidazolyl-5 | |
| 898 | H | H | Br | NO₂ | 4-nitroimidazolyl-5 | |
| 899 | H | H | Br | NO₂ | 2-methyl-4-nitroimidazolyl-1 | |
| 900 | H | H | Br | NO₂ | 4,5-dichloroimidazolyl-1 | |
| 901 | H | H | Br | NO₂ | 1-methylpyrryl-2 | |
| 902 | H | H | Br | NO₂ | isoxazolyl-3 | 159–162 |
| 903 | H | H | Br | NO₂ | isoxazolyl-4 | |
| 904 | H | H | Br | NO₂ | isoxazolyl-5 | 159–160 |
| 905 | H | H | Br | NO₂ | 5-chloromethylisoxazolyl-3 | |
| 906 | H | H | Br | NO₂ | isothiazolyl-3 | |
| 907 | H | H | Br | NO₂ | isothiazolyl-4 | |
| 908 | H | H | Br | NO₂ | isothiazolyl-5 | |
| 909 | H | H | Br | NO₂ | 4-methylisothiazolyl-5 | |
| 910 | H | H | Br | NO₂ | pyrazolyl-4 | |
| 911 | H | H | Br | NO₂ | pyrazolyl-5 | |
| 912 | H | H | Br | NO₂ | 4-chloropyrazolyl-5 | |
| 913 | H | H | Br | NO₂ | 1-methylpyrazolyl-5 | |
| 914 | H | H | Br | NO₂ | 1,2,3-thiadiazolyl-5 | |
| 915 | H | H | Br | NO₂ | 1,2,3-oxadiazolyl-5 | |
| 916 | H | H | Br | NO₂ | 1,2,3-oxadiazolyl-4 | |
| 917 | H | H | Br | NO₂ | 5-methyl-1,2,3-oxadiazolyl-4 | |
| 918 | H | H | Br | NO₂ | 4-methyl-1,2,3-oxadiazolyl-5 | |
| 919 | H | H | Br | NO₂ | 1,3,4-thiadiazolyl-2 | |
| 920 | H | H | Br | NO₂ | 2-methyl-1,3,4-thiadiazolyl-5 | |
| 921 | H | H | Br | NO₂ | 1,2,4-thiadiazolyl-3 | |
| 922 | H | H | Br | NO₂ | 1,2,4-thiadiazolyl-5 | |
| 923 | H | H | Br | NO₂ | 3-methyl-1,2,4-thiadiazolyl-5 | |
| 924 | H | H | Br | NO₂ | 1,2,4-oxadiazolyl-3 | |
| 925 | H | H | Br | NO₂ | 1,2,4-oxadiazolyl-5 | |
| 926 | H | H | Br | NO₂ | 1,2,4-triazolyl-5 | |
| 927 | H | H | Br | NO₂ | 1,2,4-triazolyl-3 | |
| 928 | H | H | Br | NO₂ | 1,3,4-oxadiazolyl-5 | |
| 929 | H | H | Br | NO₂ | 2-methyl-1,3,4-oxadiazolyl-5 | |
| 930 | H | H | Br | NO₂ | 2-chloro-1,3,4-oxadiazolyl-5 | |
| 931 | H | H | Br | NO₂ | 1,2,5-oxadiazolyl-3 | |
| 932 | H | H | Br | NO₂ | 3-methyl-1,2,5-oxadiazolyl-4 | |
| 933 | H | H | Br | NO₂ | 1,2,5-thiadiazolyl-3 | |
| 934 | H | H | Br | NO₂ | 3-methyl-1,2,5-thiadiazolyl-4 | |
| 935 | H | H | Br | NO₂ | 2-methylfuryl-5 | |
| 936 | H | H | Br | NO₂ | 2,5-dimethylfuryl-4 | 144–146 |
| 937 | H | H | Br | NO₂ | 2-chlorofuryl-5 | |
| 938 | H | H | Br | NO₂ | 5-methyloxazolyl-4 | |
| 939 | H | H | Br | NO₂ | 4-methyloxazolyl-2 | |
| 940 | H | H | Br | NO₂ | 2-bromofuryl-5 | |
| 941 | H | H | Br | NO₂ | 2-methylfuryl-4 | |
| 942 | H | H | Br | NO₂ | 5-methylisoxazolyl-3 | |
| 943 | H | H | Br | NO₂ | 4-methylisoxazolyl-3 | |
| 944 | H | H | Br | NO₂ | 5-methylisothiazolyl-3 | |
| 945 | H | H | Br | NO₂ | 4-methylisothiazolyl-3 | |
| 946 | H | H | Br | NO₂ | 4-methyl-1,2,3-thiadiazolyl-5 | 148–150 |
| 947 | H | H | Br | NO₂ | 5-methyl-1,2,3-thiadiazolyl-4 | |
| 948 | H | H | Br | NO₂ | pyrryl-1 | |
| 949 | H | H | Br | NO₂ | imidazolyl-1 | |
| 950 | H | H | Br | NO₂ | pyrazolyl-1 | |
| 951 | H | H | Br | NO₂ | 1,3,4-triazolyl-1 | |
| 952 | H | H | Br | NO₂ | 1,2,4-triazolyl-1 | |

-continued

| No. | R¹ | R² | R³ | R⁴ | R⁵ | m.p. [°C.] |
|---|---|---|---|---|---|---|
| 953 | H | H | Br | H | thenyl-2 | |
| 954 | H | H | Br | H | thenyl-3 | |
| 955 | H | H | Br | H | 2-chlorothenyl-3 | |
| 956 | H | H | Br | H | 5-chlorothenyl-2 | |
| 957 | H | H | Br | H | 5-nitrothenyl-2 | |
| 958 | H | H | Br | H | 4-methylthenyl-2 | |
| 959 | H | H | Br | H | 3-methylthenyl-2 | |
| 960 | H | H | Br | H | 2-methylthenyl-3 | |
| 961 | H | H | Br | H | 3-methylthenyl-4 | |
| 962 | H | H | Br | H | 2,5-dimethylthenyl-4 | |
| 963 | H | H | Br | H | 2,3-dichlorothenyl-4 | |
| 964 | H | H | Br | H | 5-methylthenyl-2 | |
| 965 | H | H | Br | H | pyrryl-2 | |
| 966 | H | H | Br | H | pyrryl-3 | |
| 967 | H | H | Br | H | 3-methylpyrryl-2 | |
| 968 | H | H | Br | H | 2-methylpyrryl-3 | |
| 969 | H | H | Br | H | 5-chloropyrryl-2 | |
| 970 | H | H | Br | H | oxazolyl-2 | |
| 971 | H | H | Br | H | oxazolyl-4 | |
| 972 | H | H | Br | H | oxazolyl-5 | |
| 973 | H | H | Br | H | 1,2,3-thiadiazolyl-4 | 158–159 |
| 974 | H | H | Br | H | 4-methyloxazolyl-5 | |
| 975 | H | H | Br | H | 2-methyloxazolyl-5 | |
| 976 | H | H | Br | H | thiazolyl-2 | |
| 977 | H | H | Br | H | thiazolyl-4 | |
| 978 | H | H | Br | H | thiazolyl-5 | |
| 979 | H | H | Br | H | 4-methylthiazolyl-5 | |
| 980 | H | H | Br | H | 2-methylthiazolyl-5 | |
| 981 | H | H | Br | H | imidazolyl-4 | |
| 982 | H | H | Br | H | imidazolyl-5 | |
| 983 | H | H | Br | H | 4-methylimidazolyl-5 | |
| 984 | H | H | Br | H | 1-methylimidazolyl-5 | |
| 985 | H | H | Br | H | 4-nitroimidazolyl-1 | |
| 986 | H | H | Br | H | 2-methyl-4-nitroimidazolyl-1 | |
| 987 | H | H | Br | H | 4,5-dichloroimidazolyl-1 | |
| 988 | H | H | Br | H | 1-methylpyrryl-2 | |
| 989 | H | H | Br | H | isoxazolyl-3 | 128–129 |
| 990 | H | H | Br | H | isoxazolyl-4 | |
| 991 | H | H | Br | H | isoxazolyl-5 | 135–137 |
| 992 | H | H | Br | H | 5-chloromethylisoxazolyl-3 | 134–136 |
| 993 | H | H | Br | H | isothiazolyl-3 | |
| 994 | H | H | Br | H | isothiazolyl-4 | |
| 995 | H | H | Br | H | isothiazolyl-5 | |
| 996 | H | H | Br | H | 4-methylisothiazolyl-5 | |
| 997 | H | H | Br | H | pyrazolyl-4 | |
| 998 | H | H | Br | H | pyrazolyl-5 | |
| 999 | H | H | Br | H | 4-chloropyrazolyl-5 | |
| 1000 | H | H | Br | H | 1-methylpyrazolyl-5 | |
| 1001 | H | H | Br | H | 1,2,3-thiadiazolyl-5 | |
| 1002 | H | H | Br | H | 1,2,3-oxadiazolyl-5 | |
| 1003 | H | H | Br | H | 1,2,3-oxadiazolyl-4 | |
| 1004 | H | H | Br | H | 5-methyl-1,2,3-oxadiazolyl-4 | |
| 1005 | H | H | Br | H | 4-methyl-1,2,3-oxadiazolyl-5 | |
| 1006 | H | H | Br | H | 1,3,4-thiadiazolyl-2 | |
| 1007 | H | H | Br | H | 2-methyl-1,3,4-thiadiazolyl-5 | |
| 1008 | H | H | Br | H | 1,2,4-thiadiazolyl-3 | |
| 1009 | H | H | Br | H | 1,2,4-thiadiazolyl-5 | |
| 1010 | H | H | Br | H | 3-methyl-1,2,4-thiadiazolyl-5 | |
| 1011 | H | H | Br | H | 1,2,4-oxadiazolyl-3 | |
| 1012 | H | H | Br | H | 1,2,4-oxadiazolyl-5 | |
| 1013 | H | H | Br | H | 1,2,4-triazolyl-5 | |
| 1014 | H | H | Br | H | 1,2,4-triazolyl-3 | |
| 1015 | H | H | Br | H | 1,3,4-oxadiazolyl-5 | |
| 1016 | H | H | Br | H | 2-methyl-1,3,4-oxadiazolyl-5 | |
| 1017 | H | H | Br | H | 2-chloro-1,3,4-oxadiazolyl-5 | |
| 1018 | H | H | Br | H | 1,2,5-oxadiazolyl-3 | |
| 1019 | H | H | Br | H | 3-methyl-1,2,5-oxadiazolyl-4 | |
| 1020 | H | H | Br | H | 1,2,5-thiadiazolyl-3 | |
| 1021 | H | H | Br | H | 3-methyl-1,2,5-thiadiazolyl-4 | |
| 1022 | H | H | Br | H | 2-methylfuryl-5 | |
| 1023 | H | H | Br | H | 2,5-dimethylfuryl-4 | 116–117 |
| 1024 | H | H | Br | H | 2-chlorofuryl-5 | |
| 1025 | H | H | Br | H | 5-methyloxazolyl-4 | |
| 1026 | H | H | Br | H | 4-methyloxazolyl-2 | |
| 1027 | H | H | Br | H | 2-bromofuryl-5 | |
| 1028 | H | H | Br | H | 2-methylfuryl-4 | |
| 1029 | H | H | Br | H | 5-methylisoxazolyl-3 | |
| 1030 | H | H | Br | H | 4-methylisoxazolyl-3 | |
| 1031 | H | H | Br | H | 5-methylisothiazolyl-3 | |
| 1032 | H | H | Br | H | 4-methylisothiazolyl-3 | |
| 1033 | H | H | Br | H | 4-methyl-1,2,3-thiadiazolyl-5 | 120–121 |

-continued

| No. | R¹ | R² | R³ | R⁴ | R⁵ | m.p. [°C.] |
|---|---|---|---|---|---|---|
| 1034 | H | H | Br | H | 5-methyl-1,2,3-thiadiazolyl-4 | |
| 1035 | H | H | Br | H | pyrryl-1 | |
| 1036 | H | H | Br | H | imidazolyl-1 | |
| 1037 | H | H | Br | H | pyrazolyl-1 | |
| 1038 | H | H | Br | H | 1,3,4-triazolyl-1 | |
| 1039 | H | H | Br | H | 1,2,4-triazolyl-1 | |
| 1040 | CH₃ | H | NO₂ | NO₂ | thenyl-2 | |
| 1041 | CH₃ | H | NO₂ | NO₂ | thenyl-3 | |
| 1042 | CH₃ | H | NO₂ | NO₂ | 2,5-dimethylthenyl-4 | |
| 1043 | CH₃ | H | NO₂ | NO₂ | 5-methylthenyl-2 | |
| 1044 | CH₃ | H | NO₂ | NO₂ | pyrryl-2 | |
| 1045 | CH₃ | H | NO₂ | NO₂ | pyrryl-3 | |
| 1046 | CH₃ | H | NO₂ | NO₂ | oxazolyl-2 | |
| 1047 | CH₃ | H | NO₂ | NO₂ | oxazolyl-4 | |
| 1048 | CH₃ | H | NO₂ | NO₂ | oxazolyl-5 | |
| 1049 | CH₃ | H | NO₂ | NO₂ | 1,2,3-thiadiazolyl-4 | |
| 1050 | CH₃ | H | NO₂ | NO₂ | 4-methyloxazolyl-5 | |
| 1051 | CH₃ | H | NO₂ | NO₂ | thiazolyl-2 | |
| 1052 | CH₃ | H | NO₂ | NO₂ | thiazolyl-4 | |
| 1053 | CH₃ | H | NO₂ | NO₂ | thiazolyl-5 | |
| 1054 | CH₃ | H | NO₂ | NO₂ | 4-methylthiazolyl-5 | |
| 1055 | CH₃ | H | NO₂ | NO₂ | imidazolyl-4 | |
| 1056 | CH₃ | H | NO₂ | NO₂ | imidazolyl-5 | |
| 1057 | CH₃ | H | NO₂ | NO₂ | 4-methylimidazolyl-5 | |
| 1058 | CH₃ | H | NO₂ | NO₂ | 1-methylimidazolyl-5 | |
| 1059 | CH₃ | H | NO₂ | NO₂ | 4-nitroimidazolyl-1 | |
| 1060 | CH₃ | H | NO₂ | NO₂ | 2-methyl-4-nitroimidazolyl-1 | |
| 1061 | CH₃ | H | NO₂ | NO₂ | 4,5-dichloroimidazolyl-1 | |
| 1062 | CH₃ | H | NO₂ | NO₂ | 1-methylpyrryl-2 | |
| 1063 | CH₃ | H | NO₂ | NO₂ | isoxazolyl-3 | |
| 1064 | CH₃ | H | NO₂ | NO₂ | isoxazolyl-4 | |
| 1065 | CH₃ | H | NO₂ | NO₂ | isoxazolyl-5 | |
| 1066 | CH₃ | H | NO₂ | NO₂ | 5-chloromethylisoxazolyl-3 | |
| 1067 | CH₃ | H | NO₂ | NO₂ | isothiazolyl-3 | |
| 1068 | CH₃ | H | NO₂ | NO₂ | isothiazolyl-4 | |
| 1069 | CH₃ | H | NO₂ | NO₂ | isothiazolyl-5 | |
| 1070 | CH₃ | H | NO₂ | NO₂ | 4-methylisothiazolyl-5 | |
| 1071 | CH₃ | H | NO₂ | NO₂ | pyrazolyl-4 | |
| 1072 | CH₃ | H | NO₂ | NO₂ | pyrazolyl-5 | |
| 1073 | CH₃ | H | NO₂ | NO₂ | 1-methylpyrazolyl-5 | |
| 1074 | CH₃ | H | NO₂ | NO₂ | 1,2,3-thiadiazolyl-5 | |
| 1075 | CH₃ | H | NO₂ | NO₂ | 1,2,3-oxadiazolyl-5 | |
| 1076 | CH₃ | H | NO₂ | NO₂ | 1,2,3-oxadiazolyl-4 | |
| 1077 | CH₃ | H | NO₂ | NO₂ | 5-methyl-1,2,3-oxadiazolyl-4 | |
| 1078 | CH₃ | H | NO₂ | NO₂ | 4-methyl-1,2,3-oxadiazolyl-5 | |
| 1079 | CH₃ | H | NO₂ | NO₂ | 1,3,4-thiadiazolyl-2 | |
| 1080 | CH₃ | H | NO₂ | NO₂ | 2-methyl-1,3,4-thiadiazolyl-5 | |
| 1081 | CH₃ | H | NO₂ | NO₂ | 1,2,4-thiadiazolyl-3 | |
| 1082 | CH₃ | H | NO₂ | NO₂ | 1,2,4-thiadiazolyl-5 | |
| 1083 | CH₃ | H | NO₂ | NO₂ | 3-methyl-1,2,4-thiadiazolyl-5 | |
| 1084 | CH₃ | H | NO₂ | NO₂ | 1,2,4-oxadiazolyl-3 | |
| 1085 | CH₃ | H | NO₂ | NO₂ | 1,2,4-oxadiazolyl-5 | |
| 1086 | CH₃ | H | NO₂ | NO₂ | 1,2,4-triazolyl-5 | |
| 1087 | CH₃ | H | NO₂ | NO₂ | 1,2,4-triazolyl-3 | |
| 1088 | CH₃ | H | NO₂ | NO₂ | 1,3,4-oxadiazolyl-5 | |
| 1089 | CH₃ | H | NO₂ | NO₂ | 2-methyl-1,3,4-oxadiazolyl-5 | |
| 1090 | CH₃ | H | NO₂ | NO₂ | 1,2,5-oxadiazolyl-3 | |
| 1091 | CH₃ | H | NO₂ | NO₂ | 3-methyl-1,2,5-oxadiazolyl-4 | |
| 1092 | CH₃ | H | NO₂ | NO₂ | 1,2,5-thiadiazolyl-3 | |
| 1093 | CH₃ | H | NO₂ | NO₂ | 3-methyl-1,2,5-thiadiazolyl-4 | |
| 1094 | CH₃ | H | NO₂ | NO₂ | 2-methylfuryl-5 | |
| 1095 | CH₃ | H | NO₂ | NO₂ | 2,5-dimethylfuryl-4 | 156–160 |
| 1096 | CH₃ | H | NO₂ | NO₂ | 2-chlorofuryl-5 | |
| 1097 | CH₃ | H | NO₂ | NO₂ | 5-methyloxazolyl-4 | |
| 1098 | CH₃ | H | NO₂ | NO₂ | 4-methyloxazolyl-2 | |
| 1099 | CH₃ | H | NO₂ | NO₂ | 5-methylisoxazolyl-3 | |
| 1100 | CH₃ | H | NO₂ | NO₂ | 4-methylisoxazolyl-3 | |
| 1101 | CH₃ | H | NO₂ | NO₂ | 5-methylisothiazolyl-3 | |
| 1102 | CH₃ | H | NO₂ | NO₂ | 4-methylisothiazolyl-3 | |
| 1103 | CH₃ | H | NO₂ | NO₂ | 4-methyl-1,2,3-thiadiazolyl-5 | |
| 1104 | CH₃ | H | NO₂ | NO₂ | 5-methyl-1,2,3-thiadiazolyl-4 | |
| 1105 | CH₃ | H | NO₂ | NO₂ | pyrryl-1 | |
| 1106 | CH₃ | H | NO₂ | NO₂ | imidazolyl-1 | |
| 1107 | CH₃ | H | NO₂ | NO₂ | pyrazolyl-1 | |
| 1108 | CH₃ | H | NO₂ | NO₂ | 1,3,4-triazolyl-1 | |
| 1109 | CH₃ | H | NO₂ | NO₂ | 1,2,4-triazolyl-1 | |
| 1110 | CH₃ | H | NO₂ | Cl | thenyl-2 | |
| 1111 | CH₃ | H | NO₂ | Cl | thenyl-3 | |
| 1112 | CH₃ | H | NO₂ | Cl | 2,5-dimethylthenyl-4 | |
| 1113 | CH₃ | H | NO₂ | Cl | 5-methylthenyl-2 | |
| 1114 | CH₃ | H | NO₂ | Cl | pyrryl-2 | |

-continued

| No. | R¹ | R² | R³ | R⁴ | R⁵ | m.p. [°C.] |
|---|---|---|---|---|---|---|
| 1115 | CH₃ | H | NO₂ | Cl | pyrryl-3 | |
| 1116 | CH₃ | H | NO₂ | Cl | oxazolyl-2 | |
| 1117 | CH₃ | H | NO₂ | Cl | oxazolyl-4 | |
| 1118 | CH₃ | H | NO₂ | Cl | oxazolyl-5 | |
| 1119 | CH₃ | H | NO₂ | Cl | 1,2,3-thiadiazolyl-4 | |
| 1120 | CH₃ | H | NO₂ | Cl | 4-methyloxazolyl-5 | |
| 1121 | CH₃ | H | NO₂ | Cl | thiazolyl-2 | |
| 1122 | CH₃ | H | NO₂ | Cl | thiazolyl-4 | |
| 1123 | CH₃ | H | NO₂ | Cl | thiazolyl-5 | |
| 1124 | CH₃ | H | NO₂ | Cl | 4-methylthiazolyl-5 | |
| 1125 | CH₃ | H | NO₂ | Cl | imidazolyl-4 | |
| 1126 | CH₃ | H | NO₂ | Cl | imidazolyl-5 | |
| 1127 | CH₃ | H | NO₂ | Cl | 4-methylimidazolyl-5 | |
| 1128 | CH₃ | H | NO₂ | Cl | 1-methylimidazolyl-5 | |
| 1129 | CH₃ | H | NO₂ | Cl | 4-nitroimidazolyl-1 | |
| 1130 | CH₃ | H | NO₂ | Cl | 2-methyl-4-nitroimidazolyl-1 | |
| 1131 | CH₃ | H | NO₂ | Cl | 4,5-dichloroimidazolyl-1 | |
| 1132 | CH₃ | H | NO₂ | Cl | 1-methylpyrryl-2 | |
| 1133 | CH₃ | H | NO₂ | Cl | isoxazolyl-3 | |
| 1134 | CH₃ | H | NO₂ | Cl | isoxazolyl-4 | |
| 1135 | CH₃ | H | NO₂ | Cl | isoxazolyl-5 | |
| 1136 | CH₃ | H | NO₂ | Cl | 5-chloromethylisoxazolyl-3 | |
| 1137 | CH₃ | H | NO₂ | Cl | isothiazolyl-3 | |
| 1138 | CH₃ | H | NO₂ | Cl | isothiazolyl-4 | |
| 1139 | CH₃ | H | NO₂ | Cl | isothiazolyl-5 | |
| 1140 | CH₃ | H | NO₂ | Cl | 4-methylisothiazolyl-5 | |
| 1141 | CH₃ | H | NO₂ | Cl | pyrazolyl-4 | |
| 1142 | CH₃ | H | NO₂ | Cl | pyrazolyl-5 | |
| 1143 | CH₃ | H | NO₂ | Cl | 1-methylpyrazolyl-5 | |
| 1144 | CH₃ | H | NO₂ | Cl | 1,2,3-thiadiazolyl-5 | |
| 1145 | CH₃ | H | NO₂ | Cl | 1,2,3-oxadiazolyl-5 | |
| 1146 | CH₃ | H | NO₂ | Cl | 1,2,3-oxadiazolyl-4 | |
| 1147 | CH₃ | H | NO₂ | Cl | 5-methyl-1,2,3-oxadiazolyl-4 | |
| 1148 | CH₃ | H | NO₂ | Cl | 4-methyl-1,2,3-oxadiazolyl-5 | |
| 1149 | CH₃ | H | NO₂ | Cl | 1,3,4-thiadiazolyl-2 | |
| 1150 | CH₃ | H | NO₂ | Cl | 2-methyl-1,3,4-thiadiazolyl-5 | |
| 1151 | CH₃ | H | NO₂ | Cl | 1,2,4-thiadiazolyl-3 | |
| 1152 | CH₃ | H | NO₂ | Cl | 1,2,4-thiadiazolyl-5 | |
| 1153 | CH₃ | H | NO₂ | Cl | 3-methyl-1,2,4-thiadiazolyl-5 | |
| 1154 | CH₃ | H | NO₂ | Cl | 1,2,4-oxadiazolyl-3 | |
| 1155 | CH₃ | H | NO₂ | Cl | 1,2,4-oxadiazolyl-5 | |
| 1156 | CH₃ | H | NO₂ | Cl | 1,2,4-triazolyl-5 | |
| 1157 | CH₃ | H | NO₂ | Cl | 1,2,4-triazolyl-3 | |
| 1158 | CH₃ | H | NO₂ | Cl | 1,3,4-oxadiazolyl-5 | |
| 1159 | CH₃ | H | NO₂ | Cl | 2-methyl-1,3,4-oxadiazolyl-5 | |
| 1160 | CH₃ | H | NO₂ | Cl | 1,2,5-oxadiazolyl-3 | |
| 1161 | CH₃ | H | NO₂ | Cl | 3-methyl-1,2,5-oxadiazolyl-4 | |
| 1162 | CH₃ | H | NO₂ | Cl | 1,2,5-thiadiazolyl-3 | |
| 1163 | CH₃ | H | NO₂ | Cl | 3-methyl-1,2,5-thiadiazolyl-4 | |
| 1164 | CH₃ | H | NO₂ | Cl | 2-methylfuryl-5 | |
| 1165 | CH₃ | H | NO₂ | Cl | 2,5-dimethylfuryl-4 | |
| 1166 | CH₃ | H | NO₂ | Cl | 2-chlorofuryl-5 | |
| 1167 | CH₃ | H | NO₂ | Cl | 5-methyloxazolyl-4 | |
| 1168 | CH₃ | H | NO₂ | Cl | 4-methyloxazolyl-2 | |
| 1169 | CH₃ | H | NO₂ | Cl | 5-methylisoxazolyl-3 | |
| 1170 | CH₃ | H | NO₂ | Cl | 4-methylisoxazolyl-3 | |
| 1171 | CH₃ | H | NO₂ | Cl | 5-methylisothiazolyl-3 | |
| 1172 | CH₃ | H | NO₂ | Cl | 4-methylisothiazolyl-3 | |
| 1173 | CH₃ | H | NO₂ | Cl | 4-methyl-1,2,3-thiadiazolyl-5 | |
| 1174 | CH₃ | H | NO₂ | Cl | 5-methyl-1,2,3-thiadiazolyl-4 | |
| 1175 | CH₃ | H | NO₂ | Cl | pyrryl-1 | |
| 1176 | CH₃ | H | NO₂ | Cl | imidazolyl-1 | |
| 1177 | CH₃ | H | NO₂ | Cl | pyrazolyl-1 | |
| 1178 | CH₃ | H | NO₂ | Cl | 1,3,4-triazolyl-1 | |
| 1179 | CH₃ | H | NO₂ | Cl | 1,2,4-triazolyl-1 | |
| 1180 | H | H | CH₃ | NO₂ | 2,5-dimethylthenyl-4 | |
| 1181 | H | H | CH₃ | NO₂ | 5-methylthenyl-2 | |
| 1182 | H | H | CH₃ | NO₂ | pyrryl-2 | |
| 1183 | H | H | CH₃ | NO₂ | pyrryl-3 | |
| 1184 | H | H | CH₃ | NO₂ | oxazolyl-2 | |
| 1185 | H | H | CH₃ | NO₂ | oxazolyl-4 | |
| 1186 | H | H | CH₃ | NO₂ | oxazolyl-5 | |
| 1187 | H | H | CH₃ | NO₂ | 1,2,3-thiadiazolyl-4 | |
| 1188 | H | H | CH₃ | NO₂ | 4-methyloxazolyl-5 | |
| 1189 | H | H | CH₃ | NO₂ | thiazolyl-2 | |
| 1190 | H | H | CH₃ | NO₂ | thiazolyl-4 | |
| 1191 | H | H | CH₃ | NO₂ | thiazolyl-5 | |
| 1192 | H | H | CH₃ | NO₂ | 4-methylthiazolyl-5 | |
| 1193 | H | H | CH₃ | NO₂ | imidazolyl-4 | |
| 1194 | H | H | CH₃ | NO₂ | imidazolyl-5 | |
| 1195 | H | H | CH₃ | NO₂ | 4-methylimidazolyl-5 | |

-continued

| No. | R¹ | R² | R³ | R⁴ | R⁵ | m.p. [°C.] |
|---|---|---|---|---|---|---|
| 1196 | H | H | CH₃ | NO₂ | 1-methylimidazolyl-5 | |
| 1197 | H | H | CH₃ | NO₂ | 4-nitroimidazolyl-1 | |
| 1198 | H | H | CH₃ | NO₂ | 2-methyl-4-nitroimidazolyl-1 | |
| 1199 | H | H | CH₃ | NO₂ | 4,5-dichloroimidazolyl-1 | |
| 1200 | H | H | CH₃ | NO₂ | 1-methylpyrryl-2 | |
| 1201 | H | H | CH₃ | NO₂ | isoxazolyl-3 | |
| 1202 | H | H | CH₃ | NO₂ | isoxazolyl-4 | |
| 1203 | H | H | CH₃ | NO₂ | isoxazolyl-5 | |
| 1204 | H | H | CH₃ | NO₂ | 5-chloromethylisoxazolyl-3 | |
| 1205 | H | H | CH₃ | NO₂ | isothiazolyl-3 | |
| 1206 | H | H | CH₃ | NO₂ | isothiazolyl-4 | |
| 1207 | H | H | CH₃ | NO₂ | isothiazolyl-5 | |
| 1208 | H | H | CH₃ | NO₂ | 4-methylisothiazolyl-5 | |
| 1209 | H | H | CH₃ | NO₂ | pyrazolyl-4 | |
| 1210 | H | H | CH₃ | NO₂ | pyrazolyl-5 | |
| 1211 | H | H | CH₃ | NO₂ | 1-methylpyrazolyl-5 | |
| 1212 | H | H | CH₃ | NO₂ | 1,2,3-thiadiazolyl-5 | |
| 1213 | H | H | CH₃ | NO₂ | 1,2,3-oxadiazolyl-5 | |
| 1214 | H | H | CH₃ | NO₂ | 1,2,3-oxadiazolyl-4 | |
| 1215 | H | H | CH₃ | NO₂ | 5-methyl-1,2,3-oxadiazolyl-4 | |
| 1216 | H | H | CH₃ | NO₂ | 4-methyl-1,2,3-oxadiazolyl-5 | |
| 1217 | H | H | CH₃ | NO₂ | 1,3,4-thiadiazolyl-2 | |
| 1218 | H | H | CH₃ | NO₂ | 2-methyl-1,3,4-thiadiazolyl-5 | |
| 1219 | H | H | CH₃ | NO₂ | 1,2,4-thiadiazolyl-3 | |
| 1220 | H | H | CH₃ | NO₂ | 1,2,4-thiadiazolyl-5 | |
| 1221 | H | H | CH₃ | NO₂ | 3-methyl-1,2,4-thiadiazolyl-5 | |
| 1222 | H | H | CH₃ | NO₂ | 1,2,4-oxadiazolyl-3 | |
| 1223 | H | H | CH₃ | NO₂ | 1,2,4-oxadiazolyl-5 | |
| 1224 | H | H | CH₃ | NO₂ | 1,2,4-triazolyl-5 | |
| 1225 | H | H | CH₃ | NO₂ | 1,2,4-triazolyl-3 | |
| 1226 | H | H | CH₃ | NO₂ | 1,3,4-oxadiazolyl-5 | |
| 1227 | H | H | CH₃ | NO₂ | 2-methyl-1,3,4-oxadiazolyl-5 | |
| 1228 | H | H | CH₃ | NO₂ | 1,2,5-oxadiazolyl-3 | |
| 1229 | H | H | CH₃ | NO₂ | 3-methyl-1,2,5-oxadiazolyl-4 | |
| 1230 | H | H | CH₃ | NO₂ | 1,2,5-thiadiazolyl-3 | |
| 1231 | H | H | CH₃ | NO₂ | 3-methyl-1,2,5-thiadiazolyl-4 | |
| 1232 | H | H | CH₃ | NO₂ | 2-methylfuryl-5 | |
| 1233 | H | H | CH₃ | NO₂ | 2,5-dimethylfuryl-4 | |
| 1235 | H | H | CH₃ | NO₂ | 5-methyloxazolyl-4 | |
| 1234 | H | H | CH₃ | NO₂ | 4-methyloxazolyl-2 | |
| 1236 | H | H | CH₃ | NO₂ | 5-methylisoxazolyl-3 | |
| 1237 | H | H | CH₃ | NO₂ | 4-methylisoxazolyl-3 | |
| 1238 | H | H | CH₃ | NO₂ | 5-methylisothiazolyl-3 | |
| 1239 | H | H | CH₃ | NO₂ | 4-methylisothiazolyl-3 | |
| 1240 | H | H | CH₃ | NO₂ | 4-methyl-1,2,3-thiadiazolyl-5 | |
| 1241 | H | H | CH₃ | NO₂ | 5-methyl-1,2,3-thiadiazolyl-4 | |
| 1242 | H | H | CH₃ | NO₂ | pyrryl-1 | |
| 1243 | H | H | CH₃ | NO₂ | imidazolyl-1 | |
| 1244 | H | H | CH₃ | NO₂ | pyrazolyl-1 | |
| 1245 | H | H | CH₃ | NO₂ | 1,3,4-triazolyl-1 | |
| 1246 | H | H | CH₃ | NO₂ | 1,2,4-triazolyl-1 | |
| 1247 | H | H | H | I | thenyl-2 | |
| 1248 | H | H | H | I | thenyl-3 | |
| 1249 | H | H | H | I | 2,5-dimethylthenyl-4 | |
| 1250 | H | H | H | I | 5-methylthenyl-2 | |
| 1251 | H | H | H | I | pyrryl-2 | |
| 1252 | H | H | H | I | pyrryl-3 | |
| 1253 | H | H | H | I | oxazolyl-2 | |
| 1254 | H | H | H | I | oxazolyl-4 | |
| 1255 | H | H | H | I | oxazolyl-5 | |
| 1256 | H | H | H | I | 1,2,3-thiadiazolyl-4 | 177–178 |
| 1257 | H | H | H | I | 4-methyloxazolyl-5 | |
| 1258 | H | H | H | I | thiazolyl-2 | |
| 1259 | H | H | H | I | thiazolyl-4 | |
| 1260 | H | H | H | I | thiazolyl-5 | |
| 1261 | H | H | H | I | 4-methylthiazolyl-5 | |
| 1262 | H | H | H | I | imidazolyl-4 | |
| 1263 | H | H | H | I | imidazolyl-5 | |
| 1264 | H | H | H | I | 4-methylimidazolyl-5 | |
| 1265 | H | H | H | I | 1-methylimidazolyl-5 | |
| 1266 | H | H | H | I | 4-nitroimidazolyl-1 | |
| 1267 | H | H | H | I | 2-methyl-4-nitroimidazolyl-1 | |
| 1268 | H | H | H | I | 4,5-dichloroimidazolyl-1 | |
| 1269 | H | H | H | I | 1-methylpyrryl-2 | |
| 1270 | H | H | H | I | isoxazolyl-3 | 115–117 |
| 1271 | H | H | H | I | isoxazolyl-4 | |
| 1272 | H | H | H | I | isoxazolyl-5 | |
| 1273 | H | H | H | I | 5-chloromethylisoxazolyl-3 | |
| 1274 | H | H | H | I | isothiazolyl-3 | |
| 1275 | H | H | H | I | isothiazolyl-4 | |
| 1276 | H | H | H | I | isothiazolyl-5 | |

-continued

| No. | R¹ | R² | R³ | R⁴ | R⁵ | m.p. [°C.] |
|---|---|---|---|---|---|---|
| 1277 | H | H | H | I | 4-methylisothiazolyl-5 | |
| 1278 | H | H | H | I | pyrazolyl-4 | |
| 1279 | H | H | H | I | pyrazolyl-5 | |
| 1280 | H | H | H | I | 1-methylpyrazolyl-5 | |
| 1281 | H | H | H | I | 1,2,3-thiadiazolyl-5 | |
| 1282 | H | H | H | I | 1,2,3-oxadiazolyl-5 | |
| 1283 | H | H | H | I | 1,2,3-oxadiazolyl-4 | |
| 1284 | H | H | H | I | 5-methyl-1,2,3-oxadiazolyl-4 | |
| 1285 | H | H | H | I | 4-methyl-1,2,3-oxadiazolyl-5 | |
| 1286 | H | H | H | I | 1,3,4-thiadiazolyl-2 | |
| 1287 | H | H | H | I | 2-methyl-1,3,4-thiadiazolyl-5 | |
| 1288 | H | H | H | I | 1,2,4-thiadiazolyl-3 | |
| 1289 | H | H | H | I | 1,2,4-thiadiazolyl-5 | |
| 1290 | H | H | H | I | 3-methyl-1,2,4-thiadiazolyl-5 | |
| 1291 | H | H | H | I | 1,2,4-oxadiazolyl-3 | |
| 1292 | H | H | H | I | 1,2,4-oxadiazolyl-5 | |
| 1293 | H | H | H | I | 1,2,4-triazolyl-5 | |
| 1294 | H | H | H | I | 1,2,4-triazolyl-3 | |
| 1295 | H | H | H | I | 1,3,4-oxadiazolyl-5 | |
| 1296 | H | H | H | I | 2-methyl-1,3,4-oxadiazolyl-5 | |
| 1297 | H | H | H | I | 1,2,5-oxadiazolyl-3 | |
| 1298 | H | H | H | I | 3-methyl-1,2,5-oxadiazolyl-4 | |
| 1299 | H | H | H | I | 1,2,5-thiadiazolyl-3 | |
| 1300 | H | H | H | I | 3-methyl-1,2,5-thiadiazolyl-4 | |
| 1301 | H | H | H | I | 2-methylfuryl-5 | |
| 1302 | H | H | H | I | 2,5-dimethylfuryl-4 | |
| 1303 | H | H | H | I | 2-chlorofuryl-5 | |
| 1304 | H | H | H | I | 5-methyloxazolyl-4 | |
| 1305 | H | H | H | I | 4-methyloxazolyl-2 | |
| 1306 | H | H | H | I | 5-methylisoxazolyl-3 | |
| 1307 | H | H | H | I | 4-methylisoxazolyl-3 | |
| 1308 | H | H | H | I | 5-methylisothiazolyl-3 | |
| 1309 | H | H | H | I | 4-methylisothiazolyl-3 | |
| 1310 | H | H | H | I | 4-methyl-1,2,3-thiadiazolyl-5 | |
| 1311 | H | H | H | I | 5-methyl-1,2,3-thiadiazolyl-4 | |
| 1312 | H | H | H | I | pyrryl-1 | |
| 1313 | H | H | H | I | imidazolyl-1 | |
| 1314 | H | H | H | I | pyrazolyl-1 | |
| 1315 | H | H | H | I | 1,3,4-triazolyl-1 | |
| 1316 | H | H | H | I | 1,2,4-triazolyl-1 | |
| 1317 | H | H | H | F | thenyl-2 | |
| 1318 | H | H | H | F | thenyl-3 | |
| 1319 | H | H | H | F | 2,5-dimethylthenyl-4 | |
| 1320 | H | H | H | F | 5-methylthenyl-2 | |
| 1321 | H | H | H | F | pyrryl-2 | |
| 1322 | H | H | H | F | pyrryl-3 | |
| 1323 | H | H | H | F | oxazolyl-2 | |
| 1324 | H | H | H | F | oxazolyl-4 | |
| 1325 | H | H | H | F | oxazolyl-5 | |
| 1326 | H | H | H | F | 1,2,3-thiadiazolyl-4 | |
| 1327 | H | H | H | F | 4-methyloxazolyl-5 | |
| 1328 | H | H | H | F | thiazolyl-2 | |
| 1329 | H | H | H | F | thiazolyl-4 | |
| 1330 | H | H | H | F | thiazolyl-5 | |
| 1331 | H | H | H | F | 4-methylthiazolyl-5 | |
| 1332 | H | H | H | F | imidazolyl-4 | |
| 1333 | H | H | H | F | imidazolyl-5 | |
| 1334 | H | H | H | F | 4-methylimidazolyl-5 | |
| 1335 | H | H | H | F | 1-methylimidazolyl-5 | |
| 1336 | H | H | H | F | 4-nitroimidazolyl-1 | |
| 1337 | H | H | H | F | 2-methyl-4-nitroimidazolyl-1 | |
| 1338 | H | H | H | F | 4,5-dichloroimidazolyl-1 | |
| 1339 | H | H | H | F | 1-methylpyrryl-2 | |
| 1340 | H | H | H | F | isoxazolyl-3 | |
| 1341 | H | H | H | F | isoxazolyl-4 | |
| 1342 | H | H | H | F | isoxazolyl-5 | |
| 1343 | H | H | H | F | 5-chloromethylisoxazolyl-3 | |
| 1344 | H | H | H | F | isothiazolyl-3 | |
| 1345 | H | H | H | F | isothiazolyl-4 | |
| 1346 | H | H | H | F | isothiazolyl-5 | |
| 1347 | H | H | H | F | 4-methylisothiazolyl-5 | |
| 1348 | H | H | H | F | pyrazolyl-4 | |
| 1349 | H | H | H | F | pyrazolyl-5 | |
| 1350 | H | H | H | F | 1-methylpyrazolyl-5 | |
| 1351 | H | H | H | F | 1,2,3-thiadiazolyl-5 | |
| 1352 | H | H | H | F | 1,2,3-oxadiazolyl-5 | |
| 1353 | H | H | H | F | 1,2,3-oxadiazolyl-4 | |
| 1354 | H | H | H | F | 5-methyl-1,2,3-oxadiazolyl-4 | |
| 1355 | H | H | H | F | 4-methyl-1,2,3-oxadiazolyl-5 | |
| 1356 | H | H | H | F | 1,3,4-thiadiazolyl-2 | |
| 1357 | H | H | H | F | 2-methyl-1,3,4-thiadiazolyl-5 | |

-continued

| No. | R¹ | R² | R³ | R⁴ | R⁵ | m.p. [°C.] |
|---|---|---|---|---|---|---|
| 1358 | H | H | H | F | 1,2,4-thiadiazolyl-3 | |
| 1359 | H | H | H | F | 1,2,4-thiadiazolyl-5 | |
| 1360 | H | H | H | F | 3-methyl-1,2,4-thiadiazolyl-5 | |
| 1361 | H | H | H | F | 1,2,4-oxadiazolyl-3 | |
| 1362 | H | H | H | F | 1,2,4-oxadiazolyl-5 | |
| 1363 | H | H | H | F | 1,2,4-triazolyl-5 | |
| 1364 | H | H | H | F | 1,2,4-triazolyl-3 | |
| 1365 | H | H | H | F | 1,3,4-oxadiazolyl-5 | |
| 1366 | H | H | H | F | 2-methyl-1,3,4-oxadiazolyl-5 | |
| 1367 | H | H | H | F | 1,2,5-oxadiazolyl-3 | |
| 1368 | H | H | H | F | 3-methyl-1,2,5-oxadiazolyl-4 | |
| 1369 | H | H | H | F | 1,2,5-thiadiazolyl-3 | |
| 1370 | H | H | H | F | 3-methyl-1,2,5-thiadiazolyl-4 | |
| 1371 | H | H | H | F | 2-methylfuryl-5 | |
| 1372 | H | H | H | F | 2,5-dimethylfuryl-4 | |
| 1373 | H | H | H | F | 2-chlorofuryl-5 | |
| 1374 | H | H | H | F | 5-methyloxazolyl-4 | |
| 1375 | H | H | H | F | 4-methyloxazolyl-2 | |
| 1376 | H | H | H | F | 5-methylisoxazolyl-3 | |
| 1377 | H | H | H | F | 4-methylisoxazolyl-3 | |
| 1378 | H | H | H | F | 5-methylisothiazolyl-3 | |
| 1379 | H | H | H | F | 4-methylisothiazolyl-3 | |
| 1380 | H | H | H | F | 4-methyl-1,2,3-thiadiazolyl-5 | |
| 1381 | H | H | H | F | 5-methyl-1,2,3-thiadiazolyl-4 | |
| 1382 | H | H | H | F | pyrryl-1 | |
| 1383 | H | H | H | F | imidazolyl-1 | |
| 1384 | H | H | H | F | pyrazolyl-1 | |
| 1385 | H | H | H | F | 1,3,4-triazolyl-1 | |
| 1386 | H | H | H | F | 1,2,4-triazolyl-1 | |
| 1387 | H | H | NO₂ | F | thenyl-2 | |
| 1388 | H | H | NO₂ | F | thenyl-3 | |
| 1389 | H | H | NO₂ | F | 2,5-dimethylthenyl-4 | |
| 1390 | H | H | NO₂ | F | 5-methylthenyl-2 | |
| 1391 | H | H | NO₂ | F | pyrryl-2 | |
| 1392 | H | H | NO₂ | F | pyrryl-3 | |
| 1393 | H | H | NO₂ | F | oxazolyl-2 | |
| 1394 | H | H | NO₂ | F | oxazolyl-4 | |
| 1395 | H | H | NO₂ | F | oxazolyl-5 | |
| 1396 | H | H | NO₂ | F | 1,2,3-thiadiazolyl-4 | |
| 1397 | H | H | NO₂ | F | 4-methyloxazolyl-5 | |
| 1398 | H | H | NO₂ | F | thiazolyl-2 | |
| 1399 | H | H | NO₂ | F | thiazolyl-4 | |
| 1400 | H | H | NO₂ | F | thiazolyl-5 | |
| 1401 | H | H | NO₂ | F | 4-methylthiazolyl-5 | |
| 1402 | H | H | NO₂ | F | imidazolyl-4 | |
| 1403 | H | H | NO₂ | F | imidazolyl-5 | |
| 1404 | H | H | NO₂ | F | 4-methylimidazolyl-5 | |
| 1405 | H | H | NO₂ | F | 1-methylimidazolyl-5 | |
| 1406 | H | H | NO₂ | F | 4-nitroimidazolyl-5 | |
| 1407 | H | H | NO₂ | F | 2-methyl-4-nitroimidazolyl-1 | |
| 1408 | H | H | NO₂ | F | 4,5-dichloroimidazolyl-1 | |
| 1409 | H | H | NO₂ | F | 1-methylpyrryl-2 | |
| 1410 | H | H | NO₂ | F | isoxazolyl-3 | |
| 1411 | H | H | NO₂ | F | isoxazolyl-4 | |
| 1412 | H | H | NO₂ | F | isoxazolyl-5 | |
| 1413 | H | H | NO₂ | F | 5-chloromethylisoxazolyl-3 | |
| 1414 | H | H | NO₂ | F | isothiazolyl-3 | |
| 1415 | H | H | NO₂ | F | isothiazolyl-4 | |
| 1416 | H | H | NO₂ | F | isothiazolyl-5 | |
| 1417 | H | H | NO₂ | F | 4-methylisothiazolyl-5 | |
| 1418 | H | H | NO₂ | F | pyrazolyl-4 | |
| 1419 | H | H | NO₂ | F | pyrazolyl-5 | |
| 1420 | H | H | NO₂ | F | 1-methylpyrazolyl-5 | |
| 1421 | H | H | NO₂ | F | 1,2,3-thiadiazolyl-5 | |
| 1422 | H | H | NO₂ | F | 1,2,3-oxadiazolyl-5 | |
| 1423 | H | H | NO₂ | F | 1,2,3-oxadiazolyl-4 | |
| 1424 | H | H | NO₂ | F | 5-methyl-1,2,3-oxadiazolyl-4 | |
| 1425 | H | H | NO₂ | F | 4-methyl-1,2,3-oxadiazolyl-5 | |
| 1426 | H | H | NO₂ | F | 1,3,4-thiadiazolyl-2 | |
| 1427 | H | H | NO₂ | F | 2-methyl-1,3,4-thiadiazolyl-5 | |
| 1428 | H | H | NO₂ | F | 1,2,4-thiadiazolyl-3 | |
| 1429 | H | H | NO₂ | F | 1,2,4-thiadiazolyl-5 | |
| 1430 | H | H | NO₂ | F | 3-methyl-1,2,4-thiadiazolyl-5 | |
| 1431 | H | H | NO₂ | F | 1,2,4-oxadiazolyl-3 | |
| 1432 | H | H | NO₂ | F | 1,2,4-oxadiazolyl-5 | |
| 1433 | H | H | NO₂ | F | 1,2,4-triazolyl-5 | |
| 1434 | H | H | NO₂ | F | 1,2,4-triazolyl-3 | |
| 1435 | H | H | NO₂ | F | 1,3,4-oxadiazolyl-5 | |
| 1436 | H | H | NO₂ | F | 2-methyl-1,3,4-oxadiazolyl-5 | |
| 1437 | H | H | NO₂ | F | 1,2,5-oxadiazolyl-3 | |
| 1438 | H | H | NO₂ | F | 3-methyl-1,2,5-oxadiazolyl-4 | |

-continued

| No. | R¹ | R² | R³ | R⁴ | R⁵ | m.p. [°C.] |
|---|---|---|---|---|---|---|
| 1439 | H | H | NO₂ | F | 1,2,5-thiadiazolyl-3 | |
| 1440 | H | H | NO₂ | F | 3-methyl-1,2,5-thiadiazolyl-4 | |
| 1441 | H | H | NO₂ | F | 2-methylfuryl-5 | |
| 1442 | H | H | NO₂ | F | 2,5-dimethylfuryl-4 | |
| 1443 | H | H | NO₂ | F | 2-chlorofuryl-5 | |
| 1444 | H | H | NO₂ | F | 5-methyloxazolyl-4 | |
| 1445 | H | H | NO₂ | F | 4-methyloxazolyl-2 | |
| 1446 | H | H | NO₂ | F | 5-methylisoxazolyl-3 | |
| 1447 | H | H | NO₂ | F | 4-methylisoxazolyl-3 | |
| 1448 | H | H | NO₂ | F | 5-methylisothiazolyl-3 | |
| 1449 | H | H | NO₂ | F | 4-methylisothiazolyl-3 | |
| 1450 | H | H | NO₂ | F | 4-methyl-1,2,3-thiadiazolyl-5 | |
| 1451 | H | H | NO₂ | F | 5-methyl-1,2,3-thiadiazolyl-4 | |
| 1452 | H | H | NO₂ | F | pyrryl-1 | |
| 1453 | H | H | NO₂ | F | imidazolyl-1 | |
| 1454 | H | H | NO₂ | F | pyrazolyl-1 | |
| 1455 | H | H | NO₂ | F | 1,3,4-triazolyl-1 | |
| 1456 | H | H | NO₂ | F | 1,2,4-triazolyl-1 | |
| 1457 | H | H | CH₃ | Cl | 2,5-dimethylthenyl-4 | |
| 1458 | H | H | CH₃ | Cl | 5-methylthenyl-2 | |
| 1459 | H | H | CH₃ | Cl | pyrryl-2 | |
| 1460 | H | H | CH₃ | Cl | pyrryl-3 | |
| 1461 | H | H | CH₃ | Cl | oxazolyl-2 | |
| 1462 | H | H | CH₃ | Cl | oxazolyl-4 | |
| 1463 | H | H | CH₃ | Cl | oxazolyl-5 | |
| 1464 | H | H | CH₃ | Cl | 1,2,3-thiadiazolyl-4 | |
| 1465 | H | H | CH₃ | Cl | 4-methyloxazolyl-5 | |
| 1466 | H | H | CH₃ | Cl | thiazolyl-2 | |
| 1467 | H | H | CH₃ | Cl | thiazolyl-4 | |
| 1468 | H | H | CH₃ | Cl | thiazolyl-5 | |
| 1469 | H | H | CH₃ | Cl | 4-methylthiazolyl-5 | |
| 1470 | H | H | CH₃ | Cl | imidazolyl-4 | |
| 1471 | H | H | CH₃ | Cl | imidazolyl-5 | |
| 1472 | H | H | CH₃ | Cl | 4-methylimidazolyl-5 | |
| 1473 | H | H | CH₃ | Cl | 1-methylimidazolyl-5 | |
| 1474 | H | H | CH₃ | Cl | 4-nitroimidazolyl-1 | |
| 1475 | H | H | CH₃ | Cl | 2-methyl-4-nitroimidazolyl-1 | |
| 1476 | H | H | CH₃ | Cl | 4,5-dichloroimidazolyl-1 | |
| 1477 | H | H | CH₃ | Cl | 1-methylpyrryl-2 | |
| 1478 | H | H | CH₃ | Cl | isoxazolyl-3 | |
| 1479 | H | H | CH₃ | Cl | isoxazolyl-4 | |
| 1480 | H | H | CH₃ | Cl | isoxazolyl-5 | |
| 1481 | H | H | CH₃ | Cl | 5-chloromethylisoxazolyl-3 | |
| 1482 | H | H | CH₃ | Cl | isothiazolyl-3 | |
| 1483 | H | H | CH₃ | Cl | isothiazolyl-4 | |
| 1484 | H | H | CH₃ | Cl | isothiazolyl-5 | |
| 1485 | H | H | CH₃ | Cl | 4-methylisothiazolyl-5 | |
| 1486 | H | H | CH₃ | Cl | pyrazolyl-4 | |
| 1487 | H | H | CH₃ | Cl | pyrazolyl-5 | |
| 1488 | H | H | CH₃ | Cl | 1-methylpyrazolyl-5 | |
| 1489 | H | H | CH₃ | Cl | 1,2,3-thiadiazolyl-5 | |
| 1490 | H | H | CH₃ | Cl | 1,2,3-oxadiazolyl-5 | |
| 1491 | H | H | CH₃ | Cl | 1,2,3-oxadiazolyl-4 | |
| 1492 | H | H | CH₃ | Cl | 5-methyl-1,2,3-oxadiazolyl-4 | |
| 1493 | H | H | CH₃ | Cl | 4-methyl-1,2,3-oxadiazolyl-5 | |
| 1494 | H | H | CH₃ | Cl | 1,3,4-thiadiazolyl-2 | |
| 1495 | H | H | CH₃ | Cl | 2-methyl-1,3,4-thiadiazolyl-5 | |
| 1496 | H | H | CH₃ | Cl | 1,2,4-thiadiazolyl-3 | |
| 1497 | H | H | CH₃ | Cl | 1,2,4-thiadiazolyl-5 | |
| 1498 | H | H | CH₃ | Cl | 3-methyl-1,2,4-thiadiazolyl-5 | |
| 1499 | H | H | CH₃ | Cl | 1,2,4-oxadiazolyl-3 | |
| 1500 | H | H | CH₃ | Cl | 1,2,4-oxadiazolyl-5 | |
| 1501 | H | H | CH₃ | Cl | 1,2,4-triazolyl-5 | |
| 1502 | H | H | CH₃ | Cl | 1,2,4-triazolyl-3 | |
| 1503 | H | H | CH₃ | Cl | 1,3,4-oxadiazolyl-5 | |
| 1504 | H | H | CH₃ | Cl | 2-methyl-1,3,4-oxadiazolyl-5 | |
| 1505 | H | H | CH₃ | Cl | 1,2,5-oxadiazolyl-3 | |
| 1506 | H | H | CH₃ | Cl | 3-methyl-1,2,5-oxadiazolyl-4 | |
| 1507 | H | H | CH₃ | Cl | 1,2,5-thiadiazolyl-3 | |
| 1508 | H | H | CH₃ | Cl | 3-methyl-1,2,5-thiadiazolyl-4 | |
| 1509 | H | H | CH₃ | Cl | 2-methylfuryl-5 | |
| 1510 | H | H | CH₃ | Cl | 2,5-dimethylfuryl-4 | |
| 1511 | H | H | CH₃ | Cl | 2-chlorofuryl-5 | |
| 1512 | H | H | CH₃ | Cl | 5-methyloxazolyl-4 | |
| 1513 | H | H | CH₃ | Cl | 4-methyloxazolyl-2 | |
| 1514 | H | H | CH₃ | Cl | 5-methylisoxazolyl-3 | |
| 1515 | H | H | CH₃ | Cl | 4-methylisoxazolyl-2 | |
| 1516 | H | H | CH₃ | Cl | 5-methylisothiazolyl-3 | |
| 1517 | H | H | CH₃ | Cl | 4-methylisothiazolyl-3 | |
| 1518 | H | H | CH₃ | Cl | 4-methyl-1,2,3-thiadiazolyl-5 | |
| 1519 | H | H | CH₃ | Cl | 5-methyl-1,2,3-thiadiazolyl-4 | |

-continued

| No. | R¹ | R² | R³ | R⁴ | R⁵ | m.p. [°C.] |
|---|---|---|---|---|---|---|
| 1520 | H | H | CH₃ | Cl | pyrryl-1 | |
| 1521 | H | H | CH₃ | Cl | imidazolyl-1 | |
| 1522 | H | H | CH₃ | Cl | pyrazolyl-1 | |
| 1523 | H | H | CH₃ | Cl | 1,3,4-triazolyl-1 | |
| 1524 | H | H | CH₃ | Cl | 1,2,4-triazolyl-1 | |
| 1525 | H | H | I | H | thenyl-2 | |
| 1526 | H | H | I | H | thenyl-3 | |
| 1527 | H | H | I | H | 2,5-dimethylthenyl-4 | |
| 1528 | H | H | I | H | 5-methylthenyl-2 | |
| 1529 | H | H | I | H | pyrryl-2 | |
| 1530 | H | H | I | H | pyrryl-3 | |
| 1531 | H | H | I | H | oxazolyl-2 | |
| 1532 | H | H | I | H | oxazolyl-4 | |
| 1533 | H | H | I | H | oxazolyl-5 | |
| 1534 | H | H | I | H | 1,2,3-thiadiazolyl-4 | |
| 1535 | H | H | I | H | 4-methyloxazolyl-5 | |
| 1536 | H | H | I | H | thiazolyl-2 | |
| 1537 | H | H | I | H | thiazolyl-4 | |
| 1538 | H | H | I | H | thiazolyl-5 | |
| 1539 | H | H | I | H | 4-methylthiazolyl-5 | |
| 1540 | H | H | I | H | imidazolyl-4 | |
| 1541 | H | H | I | H | imidazolyl-5 | |
| 1542 | H | H | I | H | 4-methylimidazolyl-5 | |
| 1543 | H | H | I | H | 1-methylimidazolyl-5 | |
| 1544 | H | H | I | H | 4-nitroimidazolyl-1 | |
| 1545 | H | H | I | H | 2-methyl-4-nitroimidazolyl-1 | |
| 1546 | H | H | I | H | 4,5-dichloroimidazolyl-1 | |
| 1547 | H | H | I | H | 1-methylpyrryl-2 | |
| 1548 | H | H | I | H | isoxazolyl-3 | |
| 1549 | H | H | I | H | isoxazolyl-4 | |
| 1550 | H | H | I | H | isoxazolyl-5 | |
| 1551 | H | H | I | H | 5-chloromethylisoxazolyl-3 | |
| 1552 | H | H | I | H | isothiazolyl-3 | |
| 1553 | H | H | I | H | isothiazolyl-4 | |
| 1554 | H | H | I | H | isothiazolyl-5 | |
| 1555 | H | H | I | H | 4-methylisothiazolyl-5 | |
| 1556 | H | H | I | H | pyrazolyl-4 | |
| 1557 | H | H | I | H | pyrazolyl-5 | |
| 1558 | H | H | I | H | 1-methylpyrazolyl-5 | |
| 1559 | H | H | I | H | 1,2,3-thiadiazolyl-5 | |
| 1560 | H | H | I | H | 1,2,3-oxadiazolyl-5 | |
| 1561 | H | H | I | H | 1,2,3-oxadiazolyl-4 | |
| 1562 | H | H | I | H | 5-methyl-1,2,3-oxadiazolyl-4 | |
| 1563 | H | H | I | H | 4-methyl-1,2,3-oxadiazolyl-5 | |
| 1564 | H | H | I | H | 1,3,4-thiadiazolyl-2 | |
| 1565 | H | H | I | H | 2-methyl-1,3,4-thiadiazolyl-5 | |
| 1566 | H | H | I | H | 1,2,4-thiadiazolyl-3 | |
| 1567 | H | H | I | H | 1,2,4-thiadiazolyl-5 | |
| 1568 | H | H | I | H | 3-methyl-1,2,4-thiadiazolyl-5 | |
| 1569 | H | H | I | H | 1,2,4-oxadiazolyl-3 | |
| 1570 | H | H | I | H | 1,2,4-oxadiazolyl-5 | |
| 1571 | H | H | I | H | 1,2,4-triazolyl-5 | |
| 1572 | H | H | I | H | 1,2,4-triazolyl-3 | |
| 1573 | H | H | I | H | 1,3,4-oxadiazolyl-5 | |
| 1574 | H | H | I | H | 2-methyl-1,3,4-oxadiazolyl-5 | |
| 1575 | H | H | I | H | 1,2,5-oxadiazolyl-3 | |
| 1576 | H | H | I | H | 3-methyl-1,2,5-oxadiazolyl-4 | |
| 1577 | H | H | I | H | 1,2,5-thiadiazolyl-3 | |
| 1578 | H | H | I | H | 3-methyl-1,2,5-thiadiazolyl-4 | |
| 1579 | H | H | I | H | 2-methylfuryl-5 | |
| 1580 | H | H | I | H | 2,5-dimethylfuryl-4 | |
| 1581 | H | H | I | H | 2-chlorofuryl-5 | |
| 1582 | H | H | I | H | 5-methyloxazolyl-4 | |
| 1583 | H | H | I | H | 4-methyloxazolyl-2 | |
| 1584 | H | H | I | H | 5-methylisoxazolyl-3 | |
| 1585 | H | H | I | H | 4-methylisoxazolyl-3 | |
| 1586 | H | H | I | H | 5-methylisothiazolyl-3 | |
| 1587 | H | H | I | H | 4-methylisothiazolyl-3 | |
| 1588 | H | H | I | H | 4-methyl-1,2,3-thiadiazolyl-5 | |
| 1589 | H | H | I | H | 5-methyl-1,2,3-thiadiazolyl-4 | |
| 1590 | H | H | I | H | pyrryl-1 | |
| 1591 | H | H | I | H | imidazolyl-1 | |
| 1592 | H | H | I | H | pyrazolyl-1 | |
| 1593 | H | H | I | H | 1,3,4-triazolyl-1 | |
| 1594 | H | H | I | H | 1,2,4-triazolyl-1 | |
| 1595 | H | H | I | NO₂ | thenyl-2 | |
| 1596 | H | H | I | NO₂ | thenyl-3 | |
| 1597 | H | H | I | NO₂ | pyrryl-2 | |
| 1598 | H | H | I | NO₂ | pyrryl-3 | |
| 1599 | H | H | I | NO₂ | oxazolyl-2 | |
| 1600 | H | H | I | NO₂ | oxazolyl-4 | |

-continued

| No. | R¹ | R² | R³ | R⁴ | R⁵ | m.p. [°C.] |
|---|---|---|---|---|---|---|
| 1601 | H | H | I | NO₂ | 1,2,3-thiadiazolyl-4 | |
| 1602 | H | H | I | NO₂ | thiazolyl-2 | |
| 1603 | H | H | I | NO₂ | thiazolyl-4 | |
| 1604 | H | H | I | NO₂ | thiazolyl-5 | |
| 1605 | H | H | I | NO₂ | imidazolyl-4 | |
| 1606 | H | H | I | NO₂ | imidazolyl-5 | |
| 1607 | H | H | I | NO₂ | isoxazolyl-3 | |
| 1608 | H | H | I | NO₂ | isoxazolyl-4 | |
| 1609 | H | H | I | NO₂ | isoxazolyl-5 | |
| 1610 | H | H | I | NO₂ | 5-chloromethylisoxazolyl-3 | |
| 1611 | H | H | I | NO₂ | isothiazolyl-3 | |
| 1612 | H | H | I | NO₂ | isothiazolyl-4 | |
| 1613 | H | H | I | NO₂ | pyrazolyl-4 | |
| 1614 | H | H | I | NO₂ | pyrazolyl-5 | |
| 1615 | H | H | I | NO₂ | 1,2,3-thiadiazolyl-5 | |
| 1616 | H | H | I | NO₂ | 1,2,3-oxadiazolyl-5 | |
| 1617 | H | H | I | NO₂ | 1,2,3-oxadiazolyl-4 | |
| 1618 | H | H | I | NO₂ | 1,3,4-thiadiazolyl-2 | |
| 1619 | H | H | I | NO₂ | 2-methyl-1,3,4-thiadiazolyl-5 | |
| 1620 | H | H | I | NO₂ | 2-methyl-1,3,4-oxadiazolyl-5 | |
| 1621 | H | H | I | NO₂ | 2-methylfuryl-5 | |
| 1622 | H | H | I | NO₂ | 2,5-dimethylfuryl-4 | |
| 1623 | H | H | I | NO₂ | 4-methyl-1,2,3-thiadiazolyl-5 | |
| 1624 | H | H | I | NO₂ | 5-methyl-1,2,3-thiadiazolyl-4 | |
| 1625 | H | H | I | NO₂ | pyrryl-1 | |
| 1626 | H | H | I | NO₂ | imidazolyl-1 | |
| 1627 | H | H | I | NO₂ | pyrazolyl-1 | |
| 1628 | H | H | I | NO₂ | 1,3,4-triazolyl-1 | |
| 1629 | H | H | I | NO₂ | 1,2,4-triazolyl-1 | |
| 1630 | H | H | I | NO₂ | isothiazolyl-5 | |
| 1631 | H | H | F | NO₂ | thenyl-2 | |
| 1632 | H | H | F | NO₂ | thenyl-3 | |
| 1633 | H | H | F | NO₂ | pyrryl-2 | |
| 1634 | H | H | F | NO₂ | pyrryl-3 | |
| 1635 | H | H | F | NO₂ | oxazolyl-2 | |
| 1636 | H | H | F | NO₂ | oxazolyl-4 | |
| 1637 | H | H | F | NO₂ | 1,2,3-thiadiazolyl-4 | |
| 1638 | H | H | F | NO₂ | thiazolyl-2 | |
| 1639 | H | H | F | NO₂ | thiazolyl-4 | |
| 1640 | H | H | F | NO₂ | thiazolyl-5 | |
| 1641 | H | H | F | NO₂ | imidazolyl-4 | |
| 1642 | H | H | F | NO₂ | imidazolyl-5 | |
| 1643 | H | H | F | NO₂ | isoxazolyl-3 | |
| 1644 | H | H | F | NO₂ | isoxazolyl-4 | |
| 1645 | H | H | F | NO₂ | isoxazolyl-5 | |
| 1646 | H | H | F | NO₂ | 5-chloromethylisoxazolyl-3 | |
| 1647 | H | H | F | NO₂ | isothiazolyl-3 | |
| 1648 | H | H | F | NO₂ | isothiazolyl-4 | |
| 1649 | H | H | F | NO₂ | pyrazolyl-4 | |
| 1650 | H | H | F | NO₂ | pyrazolyl-5 | |
| 1651 | H | H | F | NO₂ | 1,2,3-thiadiazolyl-5 | |
| 1652 | H | H | F | NO₂ | 1,2,3-oxadiazolyl-5 | |
| 1653 | H | H | F | NO₂ | 1,2,3-oxadiazolyl-4 | |
| 1654 | H | H | F | NO₂ | 1,3,4-thiadiazolyl-2 | |
| 1655 | H | H | F | NO₂ | 2-methyl-1,3,4-thiadiazolyl-5 | |
| 1656 | H | H | F | NO₂ | 2-methyl-1,3,4-oxadiazolyl-5 | |
| 1657 | H | H | F | NO₂ | 2-methylfuryl-5 | |
| 1658 | H | H | F | NO₂ | 2,5-dimethylfuryl-4 | |
| 1659 | H | H | F | NO₂ | 4-methyl-1,2,3-thiadiazolyl-5 | |
| 1660 | H | H | F | NO₂ | 5-methyl-1,2,3-thiadiazolyl-4 | |
| 1661 | H | H | F | NO₂ | pyrryl-1 | |
| 1662 | H | H | F | NO₂ | imidazolyl-1 | |
| 1663 | H | H | F | NO₂ | pyrazolyl-1 | |
| 1664 | H | H | F | NO₂ | 1,3,4-triazolyl-1 | |
| 1665 | H | H | F | NO₂ | 1,2,4-triazolyl-1 | |
| 1666 | H | H | F | NO₂ | isothiazolyl-5 | |
| 1667 | H | H | CH₃ | H | pyrryl-2 | |
| 1668 | H | H | CH₃ | H | pyrryl-3 | |
| 1669 | H | H | CH₃ | H | oxazolyl-2 | |
| 1670 | H | H | CH₃ | H | oxazolyl-4 | |
| 1671 | H | H | CH₃ | H | 1,2,3-thiadiazolyl-4 | |
| 1672 | H | H | CH₃ | H | thiazolyl-2 | |
| 1673 | H | H | CH₃ | H | thiazolyl-4 | |
| 1674 | H | H | CH₃ | H | thiazolyl-5 | |
| 1675 | H | H | CH₃ | H | imidazolyl-4 | |
| 1676 | H | H | CH₃ | H | imidazolyl-5 | |
| 1677 | H | H | CH₃ | H | isoxazolyl-3 | 146–148 |
| 1678 | H | H | CH₃ | H | isoxazolyl-4 | |
| 1679 | H | H | CH₃ | H | isoxazolyl-5 | 129–132 |
| 1680 | H | H | CH₃ | H | 5-chloromethylisoxazolyl-3 | |
| 1681 | H | H | CH₃ | H | isothiazolyl-3 | |

-continued

| No. | R¹ | R² | R³ | R⁴ | R⁵ | m.p. [°C.] |
|---|---|---|---|---|---|---|
| 1682 | H | H | CH₃ | H | isothiazolyl-4 | |
| 1683 | H | H | CH₃ | H | pyrazolyl-4 | |
| 1684 | H | H | CH₃ | H | pyrazolyl-5 | |
| 1685 | H | H | CH₃ | H | 1,2,3-thiadiazolyl-5 | |
| 1686 | H | H | CH₃ | H | 1,2,3-oxadiazolyl-5 | |
| 1687 | H | H | CH₃ | H | 1,2,3-oxadiazolyl-4 | |
| 1688 | H | H | CH₃ | H | 1,3,4-thiadiazolyl-2 | |
| 1689 | H | H | CH₃ | H | 2-methyl-1,3,4-thiadiazolyl-5 | |
| 1690 | H | H | CH₃ | H | 2-methyl-1,3,4-oxadiazolyl-5 | |
| 1691 | H | H | CH₃ | H | 2-methylfuryl-5 | |
| 1692 | H | H | CH₃ | H | 2,5-dimethylfuryl-4 | 160–164 |
| 1693 | H | H | CH₃ | H | 4-methyl-1,2,3-thiadiazolyl-5 | 162–166 |
| 1694 | H | H | CH₃ | H | 5-methyl-1,2,3-thiadiazolyl-4 | |
| 1695 | H | H | CH₃ | H | pyrryl-1 | |
| 1696 | H | H | CH₃ | H | imidazolyl-1 | 156–158 |
| 1697 | H | H | CH₃ | H | pyrazolyl-1 | |
| 1698 | H | H | CH₃ | H | 1,3,4-triazolyl-1 | |
| 1699 | H | H | CH₃ | H | 1,2,4-triazolyl-1 | |
| 1700 | H | H | CH₃ | H | isothiazolyl-5 | |
| 1701 | CH₃ | H | H | Cl | thenyl-2 | |
| 1702 | CH₃ | H | H | Cl | thenyl-3 | |
| 1703 | CH₃ | H | H | Cl | pyrryl-2 | |
| 1704 | CH₃ | H | H | Cl | pyrryl-3 | |
| 1705 | CH₃ | H | H | Cl | oxazolyl-2 | |
| 1706 | CH₃ | H | H | Cl | oxazolyl-4 | |
| 1707 | CH₃ | H | H | Cl | 1,2,3-thiadiazolyl-4 | 127–130 |
| 1708 | CH₃ | H | H | Cl | thiazolyl-2 | |
| 1709 | CH₃ | H | H | Cl | thiazolyl-4 | |
| 1710 | CH₃ | H | H | Cl | thiazolyl-5 | |
| 1711 | CH₃ | H | H | Cl | imidazolyl-4 | |
| 1712 | CH₃ | H | H | Cl | imidazolyl-5 | |
| 1713 | CH₃ | H | H | Cl | isoxazolyl-3 | 113–117 |
| 1714 | CH₃ | H | H | Cl | isoxazolyl-4 | |
| 1715 | CH₃ | H | H | Cl | isoxazolyl-5 | 106–110 |
| 1716 | CH₃ | H | H | Cl | 5-chloromethylisoxazolyl-3 | |
| 1717 | CH₃ | H | H | Cl | isothiazolyl-3 | |
| 1718 | CH₃ | H | H | Cl | isothiazolyl-4 | |
| 1719 | CH₃ | H | H | Cl | pyrazolyl-4 | |
| 1720 | CH₃ | H | H | Cl | pyrazolyl-5 | |
| 1721 | CH₃ | H | H | Cl | 1,2,3-thiadiazolyl-5 | |
| 1722 | CH₃ | H | H | Cl | 1,2,3-oxadiazolyl-5 | |
| 1723 | CH₃ | H | H | Cl | 1,2,3-oxadiazolyl-4 | |
| 1724 | CH₃ | H | H | Cl | 1,3,4-thiadiazolyl-2 | |
| 1725 | CH₃ | H | H | Cl | 2-methyl-1,3,4-thiadiazolyl-5 | |
| 1726 | CH₃ | H | H | Cl | 2-methyl-1,3,4-oxadiazolyl-5 | |
| 1727 | CH₃ | H | H | Cl | 2-methylfuryl-5 | |
| 1728 | CH₃ | H | H | Cl | 2,5-dimethylfuryl-4 | |
| 1729 | CH₃ | H | H | Cl | 4-methyl-1,2,3-thiadiazolyl-5 | 140–142 |
| 1730 | CH₃ | H | H | Cl | 5-methyl-1,2,3-thiadiazolyl-4 | |
| 1731 | CH₃ | H | H | Cl | pyrryl-1 | |
| 1732 | CH₃ | H | H | Cl | imidazolyl-1 | |
| 1733 | CH₃ | H | H | Cl | pyrazolyl-1 | |
| 1734 | CH₃ | H | H | Cl | 1,3,4-triazolyl-1 | |
| 1735 | CH₃ | H | H | Cl | 1,2,4-triazolyl-1 | |
| 1736 | CH₃ | H | H | Cl | isothiazolyl-5 | |
| 1737 | CH₃ | H | Cl | H | thenyl-2 | |
| 1738 | CH₃ | H | Cl | H | thenyl-3 | |
| 1739 | CH₃ | H | Cl | H | pyrryl-2 | |
| 1740 | CH₃ | H | Cl | H | pyrryl-3 | |
| 1741 | CH₃ | H | Cl | H | oxazolyl-2 | |
| 1742 | CH₃ | H | Cl | H | oxazolyl-4 | |
| 1743 | CH₃ | H | Cl | H | 1,2,3-thiadiazolyl-4 | 155–157 |
| 1744 | CH₃ | H | Cl | H | thiazolyl-2 | |
| 1745 | CH₃ | H | Cl | H | thiazolyl-4 | |
| 1746 | CH₃ | H | Cl | H | thiazolyl-5 | |
| 1747 | CH₃ | H | Cl | H | imidazolyl-4 | |
| 1748 | CH₃ | H | Cl | H | imidazolyl-5 | |
| 1749 | CH₃ | H | Cl | H | isoxazolyl-3 | 128–130 |
| 1750 | CH₃ | H | Cl | H | isoxazolyl-4 | |
| 1751 | CH₃ | H | Cl | H | isoxazolyl-5 | |
| 1752 | CH₃ | H | Cl | H | 5-chloromethylisoxazolyl-3 | |
| 1753 | CH₃ | H | Cl | H | isothiazolyl-3 | |
| 1754 | CH₃ | H | Cl | H | isothiazolyl-4 | |
| 1755 | CH₃ | H | Cl | H | pyrazolyl-4 | |
| 1756 | CH₃ | H | Cl | H | pyrazolyl-5 | |
| 1757 | CH₃ | H | Cl | H | 1,2,3-thiadiazolyl-5 | |
| 1758 | CH₃ | H | Cl | H | 1,2,3-oxadiazolyl-5 | |
| 1759 | CH₃ | H | Cl | H | 1,2,3-oxadiazolyl-4 | |
| 1760 | CH₃ | H | Cl | H | 1,3,4-thiadiazolyl-2 | |
| 1761 | CH₃ | H | Cl | H | 2-methyl-1,3,4-thiadiazolyl-5 | |
| 1762 | CH₃ | H | Cl | H | 2-methyl-1,3,4-oxadiazolyl-5 | |

-continued

| No. | R¹ | R² | R³ | R⁴ | R⁵ | m.p. [°C.] |
|---|---|---|---|---|---|---|
| 1763 | CH₃ | H | Cl | H | 2-methylfuryl-5 | |
| 1764 | CH₃ | H | Cl | H | 2,5-dimethylfuryl-4 | 100–102 |
| 1765 | CH₃ | H | Cl | H | 4-methyl-1,2,3-thiadiazolyl-5 | 161–163 |
| 1766 | CH₃ | H | Cl | H | 5-methyl-1,2,3-thiadiazolyl-4 | |
| 1767 | CH₃ | H | Cl | H | pyrryl-1 | |
| 1768 | CH₃ | H | Cl | H | imidazolyl-1 | |
| 1769 | CH₃ | H | Cl | H | pyrazolyl-1 | |
| 1770 | CH₃ | H | Cl | H | 1,3,4-triazolyl-1 | |
| 1771 | CH₃ | H | Cl | H | 1,2,4-triazolyl-1 | |
| 1772 | CH₃ | H | Cl | H | isothiazolyl-5 | |
| 1773 | CH₃ | H | NO₂ | H | thenyl-2 | |
| 1774 | CH₃ | H | NO₂ | H | thenyl-3 | |
| 1775 | CH₃ | H | NO₂ | H | pyrryl-2 | |
| 1776 | CH₃ | H | NO₂ | H | pyrryl-3 | |
| 1777 | CH₃ | H | NO₂ | H | oxazolyl-2 | |
| 1778 | CH₃ | H | NO₂ | H | oxazolyl-4 | |
| 1779 | CH₃ | H | NO₂ | H | 1,2,3-thiadiazolyl-4 | |
| 1780 | CH₃ | H | NO₂ | H | thiazolyl-2 | |
| 1781 | CH₃ | H | NO₂ | H | thiazolyl-4 | |
| 1782 | CH₃ | H | NO₂ | H | thiazolyl-5 | |
| 1783 | CH₃ | H | NO₂ | H | imidazolyl-4 | |
| 1784 | CH₃ | H | NO₂ | H | imidazolyl-5 | |
| 1785 | CH₃ | H | NO₂ | H | isoxazolyl-3 | |
| 1786 | CH₃ | H | NO₂ | H | isoxazolyl-4 | |
| 1787 | CH₃ | H | NO₂ | H | isoxazolyl-5 | |
| 1788 | CH₃ | H | NO₂ | H | 5-chloromethylisoxazolyl-3 | |
| 1789 | CH₃ | H | NO₂ | H | isothiazolyl-3 | |
| 1790 | CH₃ | H | NO₂ | H | isothiazolyl-4 | |
| 1791 | CH₃ | H | NO₂ | H | pyrazolyl-4 | |
| 1792 | CH₃ | H | NO₂ | H | pyrazolyl-5 | |
| 1793 | CH₃ | H | NO₂ | H | 1,2,3-thiadiazolyl-5 | |
| 1794 | CH₃ | H | NO₂ | H | 1,2,3-oxadiazolyl-5 | |
| 1795 | CH₃ | H | NO₂ | H | 1,2,3-oxadiazolyl-4 | |
| 1796 | CH₃ | H | NO₂ | H | 1,3,4-thiadiazolyl-2 | |
| 1797 | CH₃ | H | NO₂ | H | 2-methyl-1,3,4-thiadiazolyl-5 | |
| 1798 | CH₃ | H | NO₂ | H | 2-methyl-1,3,4-oxadiazolyl-5 | |
| 1799 | CH₃ | H | NO₂ | H | 2-methylfuryl-5 | |
| 1800 | CH₃ | H | NO₂ | H | 2,5-dimethylfuryl-4 | |
| 1801 | CH₃ | H | NO₂ | H | 4-methyl-1,2,3-thiadiazolyl-5 | |
| 1802 | CH₃ | H | NO₂ | H | 5-methyl-1,2,3-thiadiazolyl-4 | |
| 1803 | CH₃ | H | NO₂ | H | pyrryl-1 | |
| 1804 | CH₃ | H | NO₂ | H | imidazolyl-1 | |
| 1805 | CH₃ | H | NO₂ | H | pyrazolyl-1 | |
| 1806 | CH₃ | H | NO₂ | H | 1,3,4-triazolyl-1 | |
| 1807 | CH₃ | H | NO₂ | H | 1,2,4-triazolyl-1 | |
| 1808 | CH₃ | H | NO₂ | H | isothiazolyl-5 | |
| 1809 | H | Cl | NO₂ | NO₂ | thenyl-2 | |
| 1810 | H | Cl | NO₂ | NO₂ | thenyl-3 | |
| 1811 | H | Cl | NO₂ | NO₂ | pyrryl-2 | |
| 1812 | H | Cl | NO₂ | NO₂ | pyrryl-3 | |
| 1813 | H | Cl | NO₂ | NO₂ | oxazolyl-2 | |
| 1814 | H | Cl | NO₂ | NO₂ | oxazolyl-4 | |
| 1815 | H | Cl | NO₂ | NO₂ | 1,2,3-thiadiazolyl-4 | |
| 1816 | H | Cl | NO₂ | NO₂ | thiazolyl-2 | |
| 1817 | H | Cl | NO₂ | NO₂ | thiazolyl-4 | |
| 1818 | H | Cl | NO₂ | NO₂ | thiazolyl-5 | |
| 1819 | H | Cl | NO₂ | NO₂ | imidazolyl-4 | |
| 1820 | H | Cl | NO₂ | NO₂ | imidazolyl-5 | |
| 1821 | H | Cl | NO₂ | NO₂ | isoxazolyl-3 | |
| 1822 | H | Cl | NO₂ | NO₂ | isoxazolyl-4 | |
| 1823 | H | Cl | NO₂ | NO₂ | isoxazolyl-5 | |
| 1824 | H | Cl | NO₂ | NO₂ | 5-chloromethylisoxazolyl-3 | |
| 1825 | H | Cl | NO₂ | NO₂ | isothiazolyl-3 | |
| 1826 | H | Cl | NO₂ | NO₂ | isothiazolyl-4 | |
| 1827 | H | Cl | NO₂ | NO₂ | pyrazolyl-4 | |
| 1828 | H | Cl | NO₂ | NO₂ | pyrazolyl-5 | |
| 1829 | H | Cl | NO₂ | NO₂ | 1,2,3-thiadiazolyl-5 | |
| 1830 | H | Cl | NO₂ | NO₂ | 1,2,3-oxadiazolyl-5 | |
| 1831 | H | Cl | NO₂ | NO₂ | 1,2,3-oxadiazolyl-4 | |
| 1832 | H | Cl | NO₂ | NO₂ | 1,3,4-thiadiazolyl-2 | |
| 1833 | H | Cl | NO₂ | NO₂ | 2-methyl-1,3,4-thiadiazolyl-5 | |
| 1834 | H | Cl | NO₂ | NO₂ | 2-methyl-1,3,4-oxadiazolyl-5 | |
| 1835 | H | Cl | NO₂ | NO₂ | 2-methylfuryl-5 | |
| 1836 | H | Cl | NO₂ | NO₂ | 2,5-dimethylfuryl-4 | |
| 1837 | H | Cl | NO₂ | NO₂ | 4-methyl-1,2,3-thiadiazolyl-5 | |
| 1838 | H | Cl | NO₂ | NO₂ | 5-methyl-1,2,3-thiadiazolyl-4 | |
| 1839 | H | Cl | NO₂ | NO₂ | pyrryl-1 | |
| 1840 | H | Cl | NO₂ | NO₂ | imidazolyl-1 | |
| 1841 | H | Cl | NO₂ | NO₂ | pyrazolyl-1 | |
| 1842 | H | Cl | NO₂ | NO₂ | 1,3,4-triazolyl-1 | |
| 1843 | H | Cl | NO₂ | NO₂ | 1,2,4-triazolyl-1 | |

-continued

| No. | $R^1$ | $R^2$ | $R^3$ | $R^4$ | $R^5$ | m.p. [°C.] |
|---|---|---|---|---|---|---|
| 1844 | H | Cl | $NO_2$ | $NO_2$ | isothiazolyl-5 | |
| 1845 | H | H | $CH_3$ | Br | 2,5-dimethylfuryl-4 | 120–122 |
| 1846 | H | H | $NO_2$ | H | 3,5-dimethylisoxazolyl-4 | 205–207 |
| 1847 | H | H | H | Cl | 3,5-dimethylisoxazolyl-4 | |
| 1848 | H | H | H | Br | 3,5-dimethylisoxazolyl-4 | |
| 1849 | H | H | H | $NO_2$ | 3,5-dimethylisoxazolyl-4 | |
| 1850 | H | H | $NO_2$ | Cl | 3,5-dimethylisoxazolyl-4 | |
| 1851 | H | H | $NO_2$ | Br | 3,5-dimethylisoxazolyl-4 | |
| 1852 | H | H | $NO_2$ | I | 3,5-dimethylisoxazolyl-4 | |
| 1853 | H | H | Cl | H | 3,5-dimethylisoxazolyl-4 | |
| 1854 | H | H | Cl | $NO_2$ | 3,5-dimethylisoxazolyl-4 | |
| 1855 | H | H | Br | $NO_2$ | 3,5-dimethylisoxazolyl-4 | |
| 1856 | H | H | Br | H | 3,5-dimethylisoxazolyl-4 | |
| 1857 | H | H | $NO_2$ | $NO_2$ | 3,5-dimethylisoxazolyl-4 | |
| 1858 | $CH_3$ | H | $NO_2$ | $NO_2$ | 3,5-dimethylisoxazolyl-4 | |
| 1859 | $CH_3$ | H | $NO_2$ | Cl | 3,5-dimethylisoxazolyl-4 | |
| 1860 | H | H | $CH_3$ | $NO_2$ | 3,5-dimethylisoxazolyl-4 | |
| 1861 | H | H | $CH_3$ | Cl | 3,5-dimethylisoxazolyl-4 | |
| 1862 | H | H | I | H | 3,5-dimethylisoxazolyl-4 | |
| 1863 | H | H | I | $NO_2$ | 3,5-dimethylisoxazolyl-4 | |
| 1864 | H | H | $CH_3$ | H | 3,5-dimethylisoxazolyl-4 | |
| 1865 | $CH_3$ | H | H | Cl | 3,5-dimethylisoxazolyl-4 | |
| 1866 | $CH_3$ | H | Cl | H | 3,5-dimethylisoxazolyl-4 | |
| 1867 | $CH_3$ | H | $NO_2$ | H | 3,5-dimethylisoxazolyl-4 | |
| 1868 | H | H | $CH_3$ | Br | isoxazolyl-3 | 138–141 |
| 1869 | H | H | $CH_3$ | Br | isoxazolyl-5 | |
| 1870 | H | H | $CH_3$ | Br | 4-methyl-1,2,3-thiadiazolyl-5 | |
| 1871 | H | H | $CH_3$ | Br | 1,2,3-thiadiazolyl-4 | 175–177 |
| 1872 | H | H | $CH_3$ | Br | 5-chloromethylisoxazolyl-3 | |

The active ingredients have a strong action on microorganisms. They prevent and heal plant diseases caused by fungi, e.g., *Botrytis cinerea* in grapes and strawberries, *Monilia fructigens* in apples, *Cercospora arachidicola* in groundnuts, *Phytophthora infestans* in potatoes and tomatoes, *Plasmopara viticola* in grapes, *Alternaria solani* in tomatoes, and *Helminthosphorium teres* and *Septoria nodorum* in cereals.

The compounds are also effective on phytopathogenic bacteria such as *Erwinia amylovora* in pears and apples, *Erwinia carotova* in potatoes, *Pseudomonas lachrymans* in cucumbers, *Pseudomonas phaseolicola* in beans, and *Xanthomonas oryzae* in rice.

Application may be effected for instance in the form of directly sprayable solutions, powders, suspensions (including high-percentage aqueous, oily or other suspensions), dispersions, emulsions, oil dispersions, pastes, dusts, broadcasting agents, or granules by spraying, admixing while stirring, trowelling, painting, impregnating, atomizing, dusting, broadcasting or watering. The forms of application depend entirely on the purpose for which the agents are being used, but they must ensure as fine a distribution of the novel active ingredients as possible.

For the preparation of solutions, emulsions and oil dispersions to be sprayed direct, mineral oil fractions of medium to high boiling point, such has kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, and particularly water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

Examples of formulations are given below.

I. 90 parts by weight of compound 1 (the compound of Example 1) is mixed with 10 parts by weight of N-methyl-alpha-pyrrolidone. A mixture is obtained which is suitable for application in the form of very fine drops.

II. 20 parts by weight of compound 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound 24 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into water and finely distributing it therein, an aqueous dispersion is obtained.

IV. 20 parts by weight of compound 43 is dissolved in a mixture consisting of 25 parts by weight of cyclohexanol, 65 parts by weight of a mineral oil fraction having a boiling point between 210 g and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound 111 is well mixed with 3 parts by weight of the sodium salt of diisobutyl-naphthalene-alpha-sulfonic acid, 10 parts by weight of the sodium salt of a lignin-sulfonic acid obtained from a sulfite waste liquor, and 7 parts by weight of powdered silica gel, and triturated in a hammer mill. By uniformly distribution the mixture in water, a spray liquor is obtained.

VI. 5 parts by weight of compound 196 is intimately mixed with 95 parts by weight of particulate kaolin. A dust is obtained containing 5% by weight of the active ingredient.

VII. 30 parts by weight of compound 214 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound 503 is intimately mixed with 30 parts of the sodium salt of a phenolsulfonic acid-urea-formaldehyde condensate, 2 parts of silica gel and 48 parts of water to give a stable aqueous dispersion.

IX. 20 parts of compound 904 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients may also be applied together with other active ingredients, e.g., herbicides, insecticides, growth regulators, and other fungicides, or in admixture with fertilizers. Mixing with other fungicides frequently results in a greater fungicidal action spectrum; with some of these fungicidal mixtures synergistic effects also occur, i.e., the fungicidal action of the combination is greater than the sum of the effects of the individual components.

The novel compounds may be employed not only in crop protection, but also for protecting various materials against degradation or destruction by bacteria or fungi. Examples of materials which can be preserved or microbicidally finished withn the novel compounds are adhesives and glues, plastics dispersions, emulsion paints, coatings in high-humidity rooms, textiles, leather, raw hides, wood and plastics, especially soft PVC.

Generally, the formulations contain from 0.1 to 95, and preferably 0.5 to 90. wt% of active ingredient. The application rates depend on the type of effect desired, and range from 0.001 to 5, preferably 0.01 to 5, wt%, based on the weight of the material to be protected; in agriculture, the rates vary from 0.1 to 5 kg/ha.

The following microorganisms, for instance, may be controlled with the compounds according to the invention in the protection of materials: *Chaetomium globosum, Chaetomium alba, Aspergillus terreus, Aspergillus niger, Aspergillus versicolor, Penicillium glaucum, Pennicilium funiculosum, Trichoderma viride, Aureobasidium pullulans, Cladosporium herbarum, Cladosporium resinae, Humicola grisea, Glenospora graphii, Phoma violacea; Streptomyces albus; Staphylococcus aureus, Escheria coli, Pseudomonas aeruginosa, Aerobactera aerogenes,* and *Serratia marcescens.*

The following list of fungicides with which the novel compounds may be combined in intended to illustrate possible combinations but not to impose any restrictions.

Examples of fungicides which may be combined with the novel compounds are:
sulfur,
dithiocarbamates and heir derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc, N,N'-ethylenebisdithiocarbamate
ammonia complex of zinc N,N'-propylenebisdithiocarbamate,
zinc N,N'-propylenebisdithioccarbamate and N,N'-polypropylenebis(thiocarbamyl) disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and diisopropyl 5-nitroisophthalate;
heterocyclic substances, such as
2-heptadecyldimidazol-2-yl acetate,
2,4-dichloro-6-(o-chloroanilino)-s-triazine,
O,O-diethyl phthalimidophosphonothioate,
5-amino-1-[-bis-(dimethylamino)-phosphinyl]-3-phenyl-1,2,4-triazole,
2,3-dicyano-1,4-dithiaanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide, N-trichloromethylthiotetrahydrophthalimide,
N-trichloromethylthiophthalimide,
N-dichlorofluoromethylthio-N',N'-dimethyl-N-phenylsulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
8-hydroxyquinoline and its copper salt,
2,3-dihydro-5-carboxanilido-6-methyl-1,4-oxathiin,
2,3-dihydro-5-carboxanilido-6-methyl-1,4-oxathiin 4,4-dioxide,
2-methyl-5,6-dihydro-5H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-cyclododecylmorpholine and its salts,
N-[3-(p-tert.butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
1-(4-phenylphenoxy)-3,3-dimethyl-1-(1H-1,2,4-triazol-1-yl)-2-butanol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
1-[bis-(4-fluorophenyl)-methylsilyl]-methyl-1H-1,2,4-triazole,
pyridine-2-mercapto-oxide,
2-[N-(3-chloro-2,6-dinitro-4-trifluoromethylphenylamino]-5-trifluoromethyl-3-chloropyridine,
1,2-bis-(3-methoxycarbonyl-2-thioureido)-benzene,
1,2-bis-(3-ethoxycarbonyl-2-thioureido)-benzene.

In the use example below, the following compounds were employed for comparison purposes:

A: 5-chloro-8-(4'-methyl-1',2',3'-thiadiazol-5'-carbonyloxy)-quinoline (EP98, 486, Example 128);
B: 8-α-furoyloxy-5-methylquinoline (British Pat. No. 1,141,697, Example 1);
C: 5-acetyl-7-nitro-8-(1',2',3'-thiadiazol-4-carbonyloxy)-quinoline (DE No. 3,225,169, Example 24);
D: 7-nitro-8-(α-thenoyloxy)-quinoline (DE No. 2,005,959, Example 38).

Use examples

Example I

Action on *Botrytis cinerea* in pimientos

Pimiento seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprinkled with a conidial suspension of the fungus *Botrytis cinerea*, and placed at 22° to 24° C. in a high-humidity chamber. After 5 days, the disease had spread to such a great extent on the untreated plants that the necroses covered the major portion of the leaves.

The compounds of Examples 1, 111, 298, 300, 301, 332, 342, 368, 384, 386, 427, 627 and 815 proved to be extremely effective and far superior to comparative agents A and D.

Example II

Action on *Phytophthora infestans* in tomatoes

Leaves of potted tomatoes of the "GroBe Fleischtomate" variety were sprayed with aqueous liquors containing (dry basis) 80% of active ingredient and 20% of emulsifier. After 24 hours the leaves were infected with a zoospore suspension of the fungus *Phytophtora infestans*. The plants were then placed for 6 days in a water vapor-saturated chamber at 16° to 18° C. After this period, the disease had spread on the untreated control plants to such an extent that the fungicidal action was able to be assessed.

The compounds of Examples 1, 2, 85, 256, 300, 301, 368, 384, 427, 469, 471 and 818 had an excellent action which was far superior to that of comparative agents A and B.

Example III

Action on *Pyrenophora teres*

Leaves of barley seedlings of the "Asse" variety, in the two-leaf stage, were sprayed on runoff with aqueous suspensions containing (dry basis) 80% of active ingredient and 20% of emulsifier. After 24 hours the plants were inoculated with a spore suspension of the fungus *Pyrenophora teres and placed for* 48 hours in a high-humidity climatic cabinet at 18° C. The plants were then cultivated for a further 5 days in the greenhouse at 20° to 22° C. and a relative humidity of 70%. The spread of the symptoms was then determined.

The compounds of Examples 85, 300, 386, 427, 973 and 1256 proved to be not only highly effective, but also far superior to comparative agent B.

Example IV

Fungicidal action on *Aspergillus niger*

The active ingredients were added, in amounts of 100, 50, 25, 10, 5 and 1 parts by weight per million parts of solution, to a nutrient solution ideally suited for promoting the growth of the fungus *Aspergillus niger*. 20 ml of the nutrient solution treated in this manner was introduced into 100 ml glass flasks and inoculated with 0.3 mg of Aspergillus spores. After the flasks had been incubated for 120 hours at 36° C., the extent of fungus spread (predominantly on the surface of the nutrient solution) was assessed.

The compounds of Examples 1, 2, 24, 43, 127, 196, 212, 214, 215, 298, 300, 342, 384, 427, 469, 471, 729, 731 and 732 had an excellent action which was far superior to that of comparative agent C.

Example V

Fungicidal action on *Aureobasidium pullulans*

To determine the action on *Aureobasidium pullulans*, the active ingredients were added, in amounts of 100, 50, 25, 12, 6, 3 and 1.5 parts by weight per million parts of solution, to a nutrient solution ideally suited for promoting the growth of the fungus. 10 ml of this mixture of nutrient solution and active ingredient was introduced into sterile test tubes and inoculated with one drop of a spore suspension containing $10^6$ conidia or cells. After 120 hours' incubation, samples were removed from those tubes showing no visible signs of fungus growth and transferred to fungus nutrient media. In this way those amounts of active ingredient were determined at which no more fungus growth occurred after transfer of a sample to the nutrient medium.

The compounds of Examples 24, 43, 74, 127, 196 and 732 were good to very good, and those of Examples 212, 214, 215, 298, 300, 342, 427, 729 and 731 excellent.

Example VI

Bactericidal action on *Staphylococcus aureus* and *Escheria coli*

The bacteria kill values were determined as follows:

5 ml of a doubly concentrated nutrient broth was added to 5 ml of a dilution of the agents in water in sterile test tubes, and mixed. The tubes were then inoculated by adding one drop of a 16-hour old broth culture (diluted 1:10) of the bacteria species *Staphylococcus aureus* and *Escheria coli*, and incubated for 24 hours at 37° C. After this time, samples were transferred from the tubes to bacteria nutrient media, which were then also incubated for 24 hours at 37° C. The dilution stage at which no bacterial growth occurred after transfer of a sample to the nutrient medium was taken as the kill value.

The compounds of Examples 2, 298, 300 and 427 were highly effective.

We claim:

1. A quinoline derivative of the formula

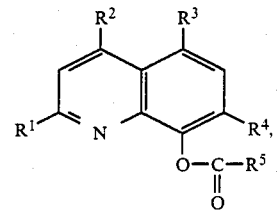

where $R^1$ is hydrogen or methyl, $R^2$ is hydrogen or halogen, $R^3$ is hydrogen, methyl, halogen or nitro, $R^4$ is hydrogen, halogen or nitro, and $R^5$ is a thiophene, pyrrole, oxazole, thiazole, imidazole, isoxazole, isothiazole, pyrazole, 1,2,3-, 1,2,4-, 1,2,5- or 1,3,4-oxadiazole or 1,2,3- or 1,2,4-triazole radical which is unsubstituted or monosubstituted or disubstituted by $C_1$-$C_4$-alkyl, $C_1$-$C_4$-haloalkyl, nitro or halogen, the substituents being independent of one another in the case of disubstitution, or is furan which is substituted by halogen or monosubstituted or disubstituted by methyl, and $R^3$ and $R^4$ are not simultaneously halogen, with the reception of 5-chloro-, 2-methyl- and 5-nitro-8-(1',2',3'-thiadiazole-4'-carbonyloxy)-quinoline, 5-chloro-8-(4'-methyl-1',2',3'-thiadiazole-4'-carbonyloxy)-quinoline, 5-methyl-, 5-methyl-7-nitro-, 5-methyl-7-halo- and 7-nitro-8-(α-thenoyloxy)-quinoline, 5-nitro- and 5-methyl-7-nitro-8-(2'-halofuroyl-5'-oxy)-quinoline and 2-methyl-8-(isoxazole-5'-carbonyloxy)-quinoline.

2. A quinoline derivative of the formula I as set forth in claim 1, where $R^1$ is hydrogen, $R^2$, $R^3$ and $R^4$ have the meanings given in claim 1, and $R^5$ is an unsubstituted or chloromethyl-substituted isoxazol-3-yl or isoxazol-5-yl radical, an unsubstituted or methyl-substituted oxazol-5-yl radical, an imidazol-1-yl radical or an unsubstituted or methyl-substituted 1,2,3-thiadiazol-4-yl or 1,2,3-thiadiazol-5-yl radical.

3. A quinoline derivative of the formula I as set forth in claim 1, where $R^1$ and $R^2$ are hydrogen, $R^3$ and $R^4$ are independent of each other and are hydrogen, halogen or nitro, and $R^5$ has the meanings given in claim 1, with the proviso that $R^3$ and $R^4$ are simultaneously neither hydrogen nor halogen.

4. A quinoline derivative of the formula I as set forth in claim 1, where $R^1$ and $R^2$ are hydrogen, $R^3$ and $R^4$ are independently of each other and are hydrogen, halogen or nitro, and $R^5$ has the meanings given in claim 2.

5. A microbicidal composition containing a carrier and an effective amount of a quinoline derivative of the formula

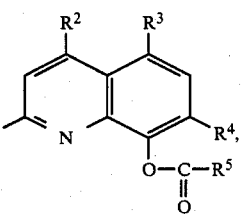

where $R^1$ is hydrogen or methyl, $R^2$ is hydrogen or halogen, $R^3$ is hydrogen, methyl, halogen or nitro, $R^4$ is hydrogen, halogen or nitro, and $R^5$ is a thiophene, pyrrole, oxazole, thiazole, imidazole, isoxazole, isothiazole, pyrazole, 1,2,3-, 1,2,4-1,2,5- or 1,3,4-oxadiazole or 1,2,3-or 1,2,4-triazole radical which is unsubstituted or monosubstituted or disubstituted by $C_1$-$C_4$-alkyl, $C_1$–$C_4$-haloalkyl, nitro or halogen, the substituents being independent of one another in the case of disubstitution, or is furan which is substituted by halogen or monosubstituted or disubstituted by methyl, and $R^3$ and $R^4$ are not simultaneously halogen, with the exception of 5-chloro-, 2-methyl- and 5-nitro-8-(1′,2′,3′-thiadiazole-4′-carbonyloxy)-quinoline, 5-chloro-8-(4′-methyl-1′,2′,3′-thiadiazole-5′-carbonyloxy)-quinoline, 5-methyl-, 5-methyl-7-nitro-, 5-metyl-7-halo-and 7-nitro-8-(α-thenoyloxy)-quinoline, 5-nitro- and 5-metyl-7-nitro-8-(2′-halofuroyl-5′-oxy)-quinoline and 2-methyl-8-(isoxazole-5′-carbonyloxy)-quinoline.

6. A process for combating bacteria or fungi, wherein an effective amount of a quinoline derivative of the formula

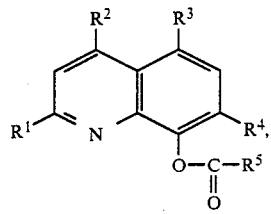

I where $R^1$ is hydrogen or methyl, $R^2$ is hydrogen or halogen, $R^3$ is hydrogen, methyl, halogen or nitro, $R^4$ is hydrogen, halogen or nitro, and $R^5$ is a thiophene, pyrrole, oxazole, thiazole, imidazole, isoxazole, isothiazole, pyrazole, 1,2,3-, 1,2,4-, 1,2,5- or 1,3,4-oxadiazole or 1,2,3- or 1,2,4-triazole radical which is unsubstituted or monosubstituted or disubstituted by $C_1$–$C_4$-alkyl, $C_1$–$C_4$-haloalkyl, nitro or halogen, the substituents being independent of one another in the case of disubstitution, or is furan which is substituted by halogen or monosubstituted or disubstituted by metyl, and $R^3$ and $R^4$ are not simultaneously halogen, with the exception of 5-chloro-, 2-methyl- and 5-nitro-8-(1′,2′,3′-thiadiazole-4′-carbonyloxy)-quinoline, 5-chloro-8-(4′-methyl-1′,2′,3′-thiadiazole-5′-carbonyloxy)-quinoline, 5-metyl-, 5-methyl-7-nitro-, 5-methyl-7-halo-and 7-nitro-8-(α-thenoyloxy)-quinoline, 5-nitro- and 5-methyl-7-nitro-8-(2′-halofuroyl-5=-oxy)-quinoline and 2-methyl-8-(isoxazole-5′-carbonyloxy)-quinoline, is allowed to act on bacteria or fungi, or on materials, soil, plants or seed threatened by bacterial or fungal attack.

7. A quinoline derivative of the formula I as set forth in claim 1, wherein $R^1$, $R^2$ and $R^4$ are each hydrogen, $R^3$ is $NO_2$ and $R^5$ is isoxazolyl-5.

* * * * *

UNITED STATES PATENT AND TRADEMARK OFFICE
CERTIFICATE OF CORRECTION

PATENT NO. : 4,829,072

DATED : May 9, 1989

INVENTOR(S) : Gergard Hamprecht, Hans Theobald, Wolfgang Spiegler, Winfried Richarz, Eberhard Ammermann, Ernst-Heinrich Pommer It is certified that error appears in the above-identified patent and that said Letters Patent is hereby corrected as shown below:

Claim 5, lines 66-67,
"pyrazole, 1,2,3-, 1,2,4-1,2,5-or 1,3,4-oxadiazole or 1,2,3-or..."

should read
--pyrazole, 1,2,3-, 1,2,4-, 1,2,5- or 1,3,4-oxadiazole or 1,2,3-or...--

Claim 6, line 22, "metyl" should read --methyl--

Claim 6, line 27, "5-metyl-" should read --5-methyl--.

Signed and Sealed this

Thirty-first Day of October, 1989

Attest:

DONALD J. QUIGG

*Attesting Officer*  *Commissioner of Patents and Trademarks*